(12) United States Patent
Jamshed et al.

(10) Patent No.: US 12,024,477 B2
(45) Date of Patent: Jul. 2, 2024

(54) BIOAUGMENTED FERTILIZER WITH ACCLIMATIZED (PREFERABLY HALOTOLERANT) EFFECTIVE MICROORGANISMS AND METHODS FOR PRODUCING THE SAME

(71) Applicant: NIHA CORP, Ontario, CA (US)

(72) Inventors: Hamad Raza Jamshed, Multan (PK); Rana Muhammad Iqbal, Multan (PK); Nasim Ahmed, Ontario, CA (US); Usama Raza, Multan (PK)

(73) Assignee: NIHA CORP, Ontario, CA (US)

( * ) Notice: Subject to any disclaimer, the term of this patent is extended or adjusted under 35 U.S.C. 154(b) by 312 days.

(21) Appl. No.: 17/231,959

(22) Filed: Apr. 15, 2021

(65) Prior Publication Data

US 2021/0371350 A1    Dec. 2, 2021

Related U.S. Application Data

(60) Provisional application No. 63/010,637, filed on Apr. 15, 2020.

(51) Int. Cl.
*C05F 11/08* (2006.01)
*C05G 5/12* (2020.01)
(Continued)

(52) U.S. Cl.
CPC ............. *C05F 11/08* (2013.01); *C05G 5/12* (2020.02); *C05G 5/38* (2020.02); *C05G 5/40* (2020.02); *C12N 1/20* (2013.01)

(58) Field of Classification Search
None
See application file for complete search history.

(56) References Cited

U.S. PATENT DOCUMENTS 3,186,826 A    6/1965  Del Muro de Rendon
3,186,828 A    6/1965  Baarson et al.
(Continued)

FOREIGN PATENT DOCUMENTS

CN           108271339 A  *  7/2018  .............. C05F 11/08
WO    WO 2010/018210 A1    2/2010
(Continued)

OTHER PUBLICATIONS

WO, PCT/US2013/033005 ISR and Written Opinion, dated Jul. 15, 2013.
(Continued)

*Primary Examiner* — Wayne A Langel
(74) *Attorney, Agent, or Firm* — One LLP

(57) ABSTRACT

The present disclosure is related to a fertilizer (inorganic/organic/natural/synthetic) enriched with acclimatized (preferably halotolerant) effective microorganisms (AEM) and optionally with an organic emulsion (OE). The present disclosure provides a bioaugmented fertilizer enriched with AEM and optionally OE. Provide product (fertilizer) specific AEM, and method for producing such fertilizers. Fertilizer enriched with AEM, OMP, and OE renders it an Integrated Plant Nutrient Management (IPNM) principles based product (fertilizer). This makes it superior in performance over conventional fertilizers (inorganic/organic/natural/synthetic) due to better nutrient use efficiency.

13 Claims, 13 Drawing Sheets

COATING/GRANULATION OF FERTILIZER WITH BIO AUGMENTED OMP & OE INNOCULATED WITH AEM AND /OR OTHER FERTILIZER

(51) Int. Cl.
  *C05G 5/30* (2020.01)
  *C05G 5/40* (2020.01)
  *C12N 1/20* (2006.01)

(56) References Cited

U.S. PATENT DOCUMENTS

| | | | |
|---|---|---|---|
| 3,234,003 | A | 2/1966 | Sawyer, Jr. et al. |
| 3,234,006 | A | 2/1966 | Sawyer, Jr. et al. |
| 3,250,607 | A | 5/1966 | Sawyer, Jr. et al. |
| 3,305,491 | A | 2/1967 | Oster |
| 3,926,841 | A | 12/1975 | Habasko et al. |
| 4,589,225 | A | 5/1986 | Stensaas |
| 5,147,441 | A | 9/1992 | Megeed |
| 5,578,486 | A | 11/1996 | Zhang |
| 5,912,398 | A | 6/1999 | Goldstein et al. |
| 8,066,793 | B2 | 11/2011 | Sinclair |
| 8,530,220 | B2 | 9/2013 | Ho et al. |
| 8,764,873 | B2 | 7/2014 | Nevin |
| 8,932,382 | B2 | 1/2015 | Tariq et al. |
| 8,932,490 | B2 | 1/2015 | Martinez et al. |
| 9,353,016 | B2 | 5/2016 | Tariq et al. |
| 9,617,190 | B2 | 4/2017 | Tariq et al. |
| 9,994,494 | B2 | 6/2018 | Tariq et al. |
| 2005/0039509 | A1 | 2/2005 | Muma |
| 2007/0131009 | A1 | 6/2007 | Westbrook et al. |
| 2008/0216534 | A1 | 9/2008 | Karr |
| 2008/0257000 | A1 | 10/2008 | McMahon et al. |
| 2010/0234222 | A1 | 9/2010 | Gidekel et al. |
| 2011/0005284 | A1 | 1/2011 | Conner et al. |
| 2011/0100078 | A1 | 5/2011 | Ho et al. |
| 2011/0283759 | A1 | 11/2011 | Cisneros et al. |
| 2014/0352376 | A1 | 12/2014 | Carpenter |
| 2016/0262389 | A1* | 9/2016 | Fagan ............ C05F 5/008 |
| 2019/0127288 | A1 | 5/2019 | Tariq et al. |
| 2020/0131096 | A1* | 4/2020 | Kanagalingam ...... C05F 17/20 |

FOREIGN PATENT DOCUMENTS

| | | | |
|---|---|---|---|
| WO | WO 2012/038740 A1 | 3/2012 | |
| WO | WO 2015/056185 A1 | 4/2015 | |
| WO | WO 2016/130586 A2 * | 8/2016 | ........... C12N 1/20 |

OTHER PUBLICATIONS

WO, PCT/US2021/027557 ISR and Written Opinion, dated Jul. 16, 2021.

Ahmad, R., et al., "Growth and Yield Response of Wheat (*Triticum aestivum* L.) and Maize (*Zea mays* L.) to Nitrogen and L-Tryptophan Enriched Compost", Pak. J. Bot., 2007, vol. 39, No. 2, pp. 541-549.

Ahmad, R., et al., "Bio-conversion of organic wastes for their recycling in agriculture: An overview of perspectives and prospects", Annals of Microbiology, 2007, vol. 57, No. 4, pp. 1-10.

Ahmad, R., et al., "Effectiveness of Organic-/Bio-Fertilizer Supplemented with Chemical Fertilizers for Improving Soil Water Retention, Aggregate Stability, Growth and Nutrient Uptake of Maize (*Zea mays* L.)", Journal of Sustainable Agriculture, 2008, vol. 31, No. 4, pp. 57-77.

Aziz, T., et al., "Phosphorus Utilization by Six *Brassica* Cultivars (*Brassica juncea* L.) From Tri-Calcium Phosphate; a Relatively Insoluble P Compound", Pak. J. Bot., 2006, vol. 38, No. 5, pp. 1529-1538.

Bhattacharyya, P., et al., "Municipal waste compost as an alternative to cattle manure for supplying potassium to lowland rice", Chemosphere, 2007, vol. 66, pp. 1789-1793.

Bhattacharyya, S.S., et al., "Effect of Balanced Fertilization on Pulse Crop Production in Red and Lateritic Soils", Better Crops, 2004, vol. 88, No. 4, pp. 25-27.

"Biofertilizer, biological fertilizer, organic fertilizer", retrieved from https://www.fao.org/3/cb5131en/online/src/html/gloss.html, 2021, 10 pages.

Bojinova, D., et al., "Solubilization of Morocco phosphorite by *Aspergillus niger*", Bioresource Technology, 2008, vol. 99, pp. 7348-7353.

Caravaca, F., et al., "Comparing the effectiveness of mycorrhizal inoculation and amendment with sugar beet, rock phosphate and *Aspergillus niger* to enhance field performance of the leguminous shrub *Dorycnium pentaphyllum* L.", Applied Soil Ecology, 2004, vol. 25, pp. 169-180.

Dastager, S. G., et al., "Isolation and characterization of novel plant growth promoting *Micrococcus* sp NII-0909 and its interaction with cowpea", Plant Physiol. Biochem., 2010, vol. 48, No. 12, pp. 987-992.

Dworkin, M., et al., "Experiments With Some Microorganisms Which Utilize Ethane and Hydrogen", Utilization of Ethane and Hydrogen, 1958, vol. 75, pp. 592-603.

"Fertilizer", retrieved from https://en.wikipedia.org/w/index.php?title=Fertilizer&oldid=930528353.com, 27 pages.

"Fertilizer Training and Modules", Food and Agriculture Organization of the United Nations, retrieved from https://www.fao.org/3/ca7496en/ca7496en.pdf, 2019, 12 pages.

Gupta, A., et al., "Role of Biofertilizers and Biopesticides for Sustainable Agriculture", 2012, Department of Biotechnology, Singhania University, Rajasthan.

Gyaneshwar, P., et al., "Effect of buffering on the phosphate-solubilizing ability of microorganisms", World Journal of Microbiology & Biotechnology, 1998, vol. 14, pp. 669-673.

Hamza, M. A., et al., "Potential and limitations of soil organic matter build-up in dry areas", African Journal of Agricultural Research, 2010, vol. 5, No. 20, pp. 2850-2861.

Harris, J. N., et al., "Laboratory tests can predict beneficial effects of phosphate-solubilising bacteria on plants", Soil Biology & Biochemistry, 2006, vol. 38, pp. 1521-1526.

Hoorman, J. J., et al., "Understanding Soil Microbes and Nutrient Recycling", Agriculture and Natural Resources, 2010, retrieved from https://ohioline.osu.edu/factsheet/SAG-16, 12 pages.

Isherwood, K.F., "Mineral Fertilizer Use and the Environment", International Fertilizer Industry Association, 2000, Paris, pp. 1-52.

Kennedy, A.C., et al., "Soil microbial diversity and the sustainability of agricultural soils", Plant and Soil, 1995, vol. 170, pp. 75-86.

Khan, M. S., et al., "Synergistic Effects of the Inoculation with Plant Growth-Promoting Rhizobacteria and an Arbuscular Mycorrhizal Fungus on the Performance of Wheat", Turk. J. Agric. For., 2007, vol. 31, pp. 355-362.

Khan, A. A., et al., "Phosphorus Solubilizing Bacteria: Occurrence, Mechanisms and their Role in Crop Production", J. Agric. Biol. Sci., 2009, vol. 1, No. 1, pp. 48-58.

Kumar, J. A., et al., "Effect of Microbial Inoculants on the Nutrient Uptake and Yield of Beetroot (*Beta vulgaris* L.)", Current Agriculture Research Journal, 2014, vol. 2, No. 2, pp. 123-130.

López-Bucio, J., et al., "The role of nutrient availability in regulating root architecture", Current Opinion in Plant Biology, 2003, vol. 6, pp. 280-287.

Lujiu, L., et al., "Balanced Fertilization Increases Garlic Yield in Anhui", Better Crops 2004, vol. 88, No. 4, pp. 30-35.

Mahdi, S. S., et al., "Bio-Fertilizers in Organic Agriculture", Journal of Phytology, 2010, vol. 2, No. 10, pp. 42-54.

Malboobi, M.A., et al., "Solubilization of organic and inorganic phosphates by three highly efficient soil bacterial isolates", World J. Microbiol. Biotechnol., 2009, vol. 25, No. 8, pp. 1471-1477.

Manzar-Ul-Alam, S., et al., "Evaluation of method and time of fertilizer application for yield and optimum P-efficiency in wheat", Songklanakarin J. Sci. Technol., 2005, vol. 27, No. 3, pp. 457-463.

Mullins, G., "Phosphorus, Agriculture & The Environment", Virginia Polytechnic Institute and State University, 2009, Publication 424-029, pp. 1-16.

Nautiyal, C. S., "An efficient microbiological growth medium for screening phosphate solubilizing microorganisms", FEMS Microbiology Letters, 1999, vol. 170, pp. 265-270.

Penrose, D. M., et al., "Methods for isolating and characterizing ACC deaminase-containing plant growth-promoting rhizobacteria", Physiologia Plantarum, 2003, vol. 118, pp. 10-15.

(56) References Cited

OTHER PUBLICATIONS

Rodríguez, H., et al., "Phosphate solubilizing bacteria and their role in plant growth promotion", Biotechnology Advances, 1999, vol. 17, pp. 319-339.

Ryan, J., et al., "Soil and Plant Analysis Laboratory Manual, Second Edition, Table of Contents", 2001, ICARDA, pp. 1-5.

Schachtman, D. P., et al., "Phosphorus Uptake by Plants: From Soil to Cell", Plant Physiol., 1998, vol. 116, pp. 447-453.

Sekhar, D.M.R., et al., "Phosphate rock with farmyard manure as P fertilizer in neutral and weakly alkaline soils", Current Science, 2001, vol. 80, No. 9, 10, pp. 1113-1115.

Semêdo, L.T.A.S., et al., "Isolation and characterization of actinomycetes from Brazilian tropical soils", Microbiol. Res., 2001, vol. 155, pp. 291-299.

Shaharoona, B., et al., "Fertilizer-dependent efficiency of Pseudomonads for improving growth, yield, and nutrient use efficiency of wheat (*Triticum aestivum* L.)", Appl. Microbiol. Biotechnol., 2008, vol. 79, pp. 147-155.

Shahzad, S.M., et al., "Screening rhizobacteria containing ACC-deaminase for growth promotion of chickpea seedlings under axenic conditions", Soil & Environ., 2010, vol. 29, No. 1, pp. 38-46.

Shenoy, V.V., et al., "Enhancing plant phosphorus use efficiency for sustainable cropping", Biotechnology Advances, 2005, vol. 23, pp. 501-513.

Takahashi, S., et al., "Wheat grain yield, phosphorus uptake and soil phosphorus fraction after 23 years of annual fertilizer application to an Andosol", Field Crops Research, 2007, vol. 101, pp. 160-171.

Tilman, D., et al., "Agricultural sustainability and intensive production practices", Nature, 2002, vol. 418, pp. 671-677.

Tripathi, S., et al., "Microbial Biomass and Its Activities in Salt-affected Coastal Soils", Biology and Fertility of Soils, 2006, vol. 42, No. 3, pp. 273-277.

United Nations Environment Programme, MAP Technical Reports Series No. 96, 1996, 132 pages.

Usherwood, N. R., et al., "Nitrogen Interactions with Phosphorus and Potassium for Optimum Crop Yield, Nitrogen Use Effectiveness, and Environmental Stewardship", The Scientific World, 2001, vol. 1, Issue S2, pp. 57-60.

Vance, C. P., et al., "Symbiotic Nitrogen Fixation and Phosphorus Acquisition. Plant Nutrition in a World of Declining Renewable Resources", Plant Physiology, 2001, vol. 127, pp. 390-397.

Vance, C. P., et al., "Phosphorus acquisition and use: critical adaptations by plants for securing a nonrenewable resource", New Phytologist, 2003, vol. 157, pp. 423-447.

Van Straaten, P., "Rocks for Crops: Agrominerals of sub-Saharan Africa", 2002, ICRAF, Nairobi, Kenya, pp. 1-348.

Vassilev, N., et al., "Biotechnological solubilization of rock phosphate on media containing agro-industrial wastes", Appl. Microbiol. Biotechnol., 2003, vol. 61, pp. 435-440.

Vitousek, P. M., et al., "Human Alteration of the Global Nitrogen Cycle: Sources and Consequences", Ecological Applications, 1997, vol. 7, No. 3, pp. 737-750.

Walpola, B. C., et al., "Prospectus of phosphate solubilizing microorganisms and phosphorus availability in agricultural soils: A review", African Journal of Microbiology Research, 2012, vol. 6, No. 37, pp. 6600-6605.

Wichern, J., et al., "Impact of salinity on soil microbial communities and the decomposition of maize in acidic soils", Geoderma, 2006, vol. 137, Nos. 1-2, pp. 100-108.

Williamson, L.C., et al., "Phosphate Availability Regulates Root System Architecture in *Arabidopsis*", Plant Physiology, 2001, vol. 126, pp. 875-882.

"Environmental, Health and Safety Guidelines for Phosphate Fertilizer Manufacturing", International Finance Corporation, World Bank Group Report, 2007, pp. 1-20.

Zou, X., et al., "A new method for estimating gross phosphorus mineralization and immobilization rates in soils", Plant and Soil, 1992, vol. 147, pp. 243-250.

Zuberer, D. A., et al., "Recovery and Enumeration of Viable Bacteria", Methods of Soil Analysis, Part 2. Microbiological and Biochemical Properties—SSSA Book Series, No. 5, Chapter 8, 1994, pp. 119-144.

\* cited by examiner

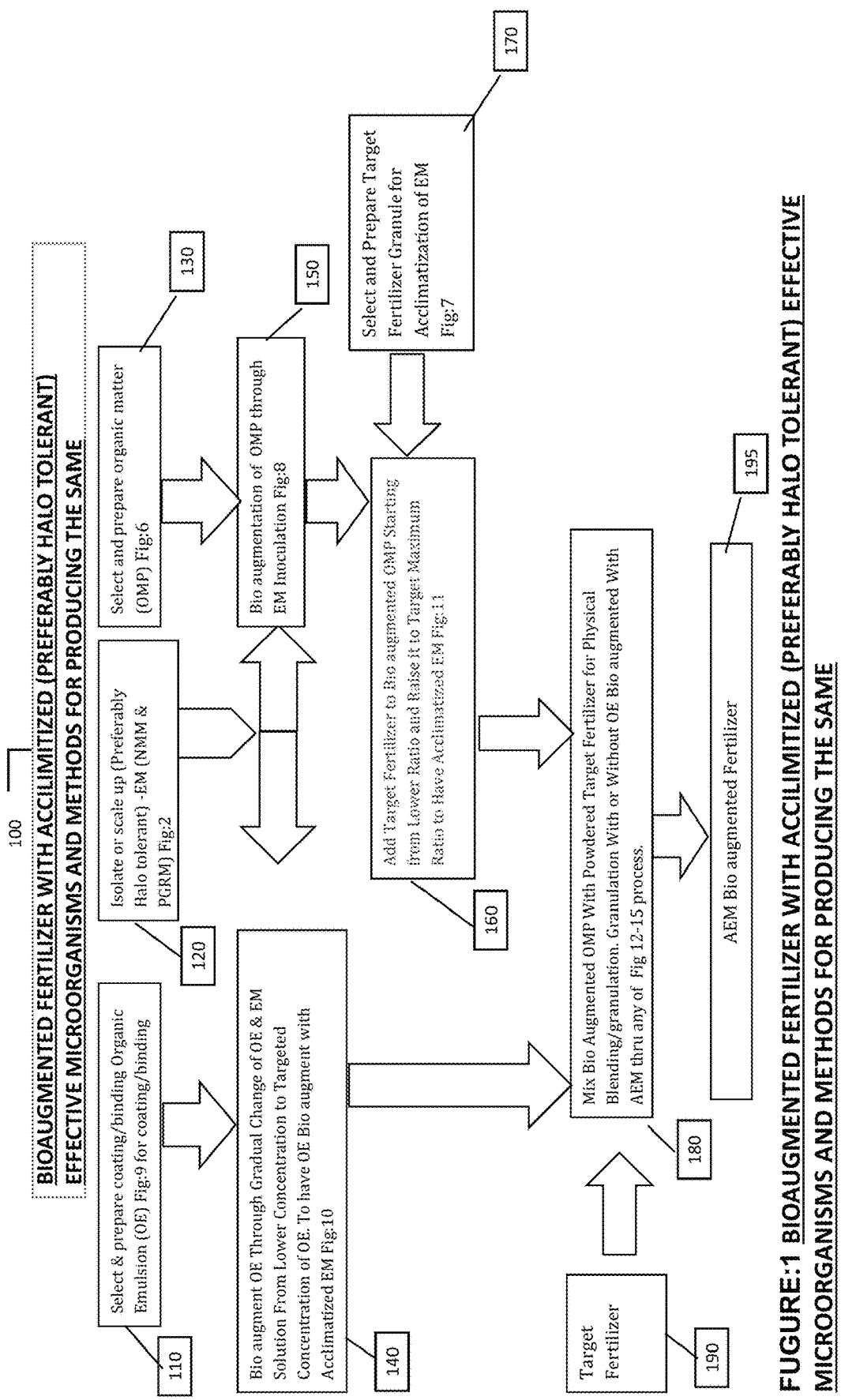
FUGURE:1 BIOAUGMENTED FERTILIZER WITH ACCILIMITIZED (PREFERABLY HALO TOLERANT) EFFECTIVE MICROORGANISMS AND METHODS FOR PRODUCING THE SAME

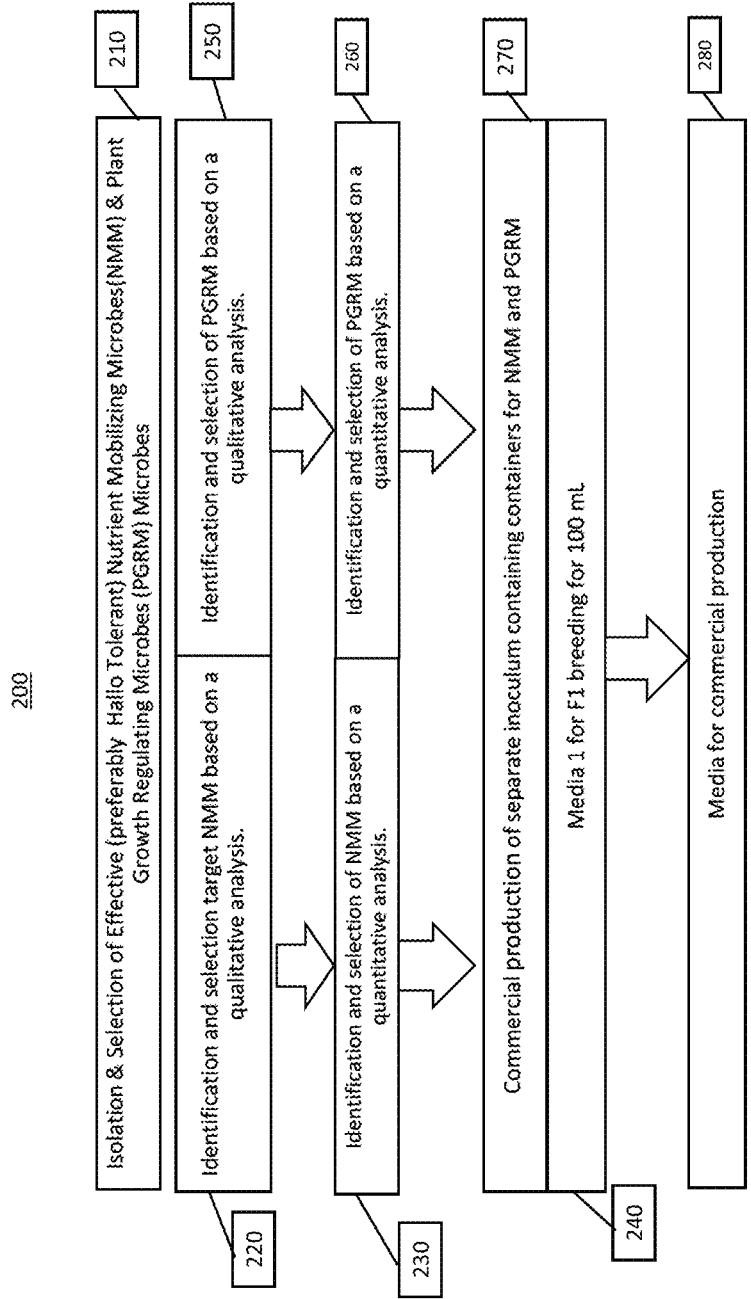
FIGURE: 2 ISOLATION & SELECTION OF EFFECTIVE (PREFERABLY HALO TOLERANT) MICROBES (NUTRIENT MOBILIZING MICROBES AND PLANT GROWTH REGULATING MICROBES)

| Media for F1 Breeding for 100 ml (Preferably Hallo Tolerant) Efficient Microbes (EM) 240 ||
|---|---|
| Ingredients | |
| Mannitol 3-4 g | $KH_2PO_4$ 0.1-0.13 g |
| Yeas Extract 0.3-0.7 g | $MgSO_4$ 0.1-0.13 g |
| Distilled Water 100 ml | $H_2SO_4$ as per need |
| | NaOH as per need |

Preparation Techniques:-

Prepare the same medium in two separate containers for NMM and PGRM. Maintain pH between 6.5 to 7. Adjust pH by adding 1M solution of either H2SO4 or NaOH. Autoclave the mixture in both the containers as per standard procedure then allow the mixture to cool to mesophylic range maintaining pH close to neutral level. Mix

FIGURE:3 MEDIA RECIPE FOR (PREFERABLY HALO TOLERANT) EFFECTIVE MICROBES F1 BREEDING

| Media for Commercial Production (EM) 280 ||||
|---|---|---|---|
| Ingredients | | | |
| Trypton | 3-4 g | Calcium Pantothinate | 0.1-0.15 g |
| Yeas Extract | 0.3-0.7 g | Vitamin B1 | 0.3-0.7 mL |
| $KH_2PO_4$ | 0.1-0.13 g | Vitamin B1 | 0.3-0.7 mL |
| $MgSO_4$ | 0.1-0.13 g | Distilled Water | 100 mL |
| | | $H_2SO_4$ as per need | |
| | | NaOH as per need | |

Preparation Techniques:-

Prepare the same medium in two separate containers for NMM and PGRM. Maintain pH between 6.5 to 7. Adjust pH by adding 1M solution of either $H_2SO_4$ or NaOH. Autoclave the mixture in both the containers as per standard procedure and then allow the mixture to cool to mesophylic range maintaining pH close to neutral level. Mix selected strains of NMM or PGRM in respective containers under aseptic conditions. Shaking should be

FIGURE:4 MEDIA RECIPE FOR (PREFERABLY HALO TOLERANT) EFFECTIVE MICROBES

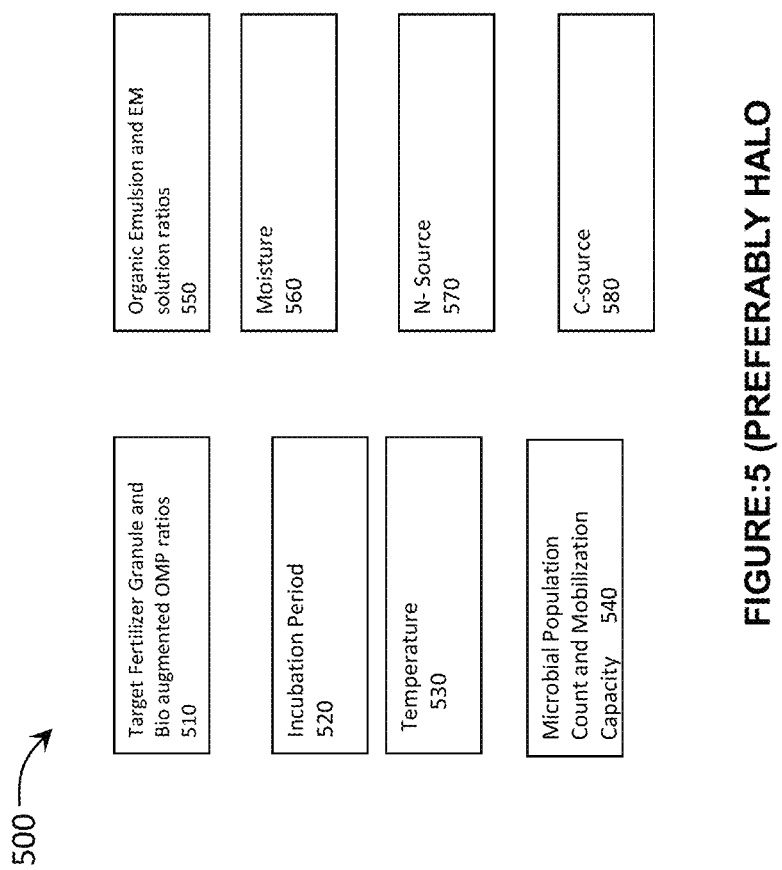
FIGURE:5 (PREFERABLY HALO TOLERANT) EM ACCLIMATIZATION CRITICAL FACTORS

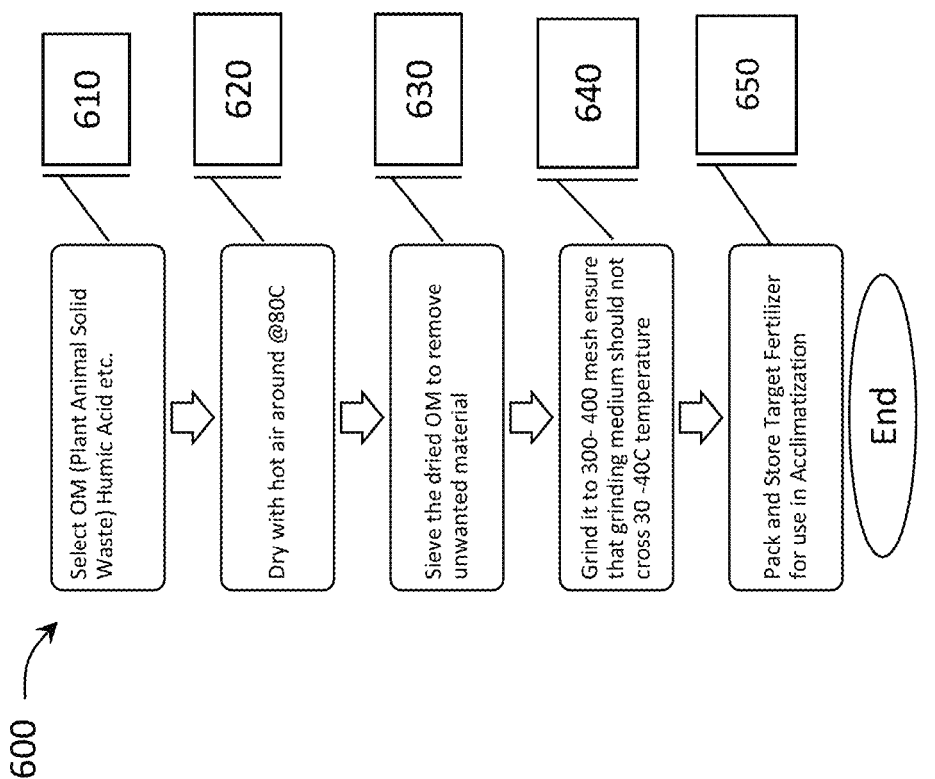
FIGURE:6 ORGANIC MATTER PREPARATION (OMP)

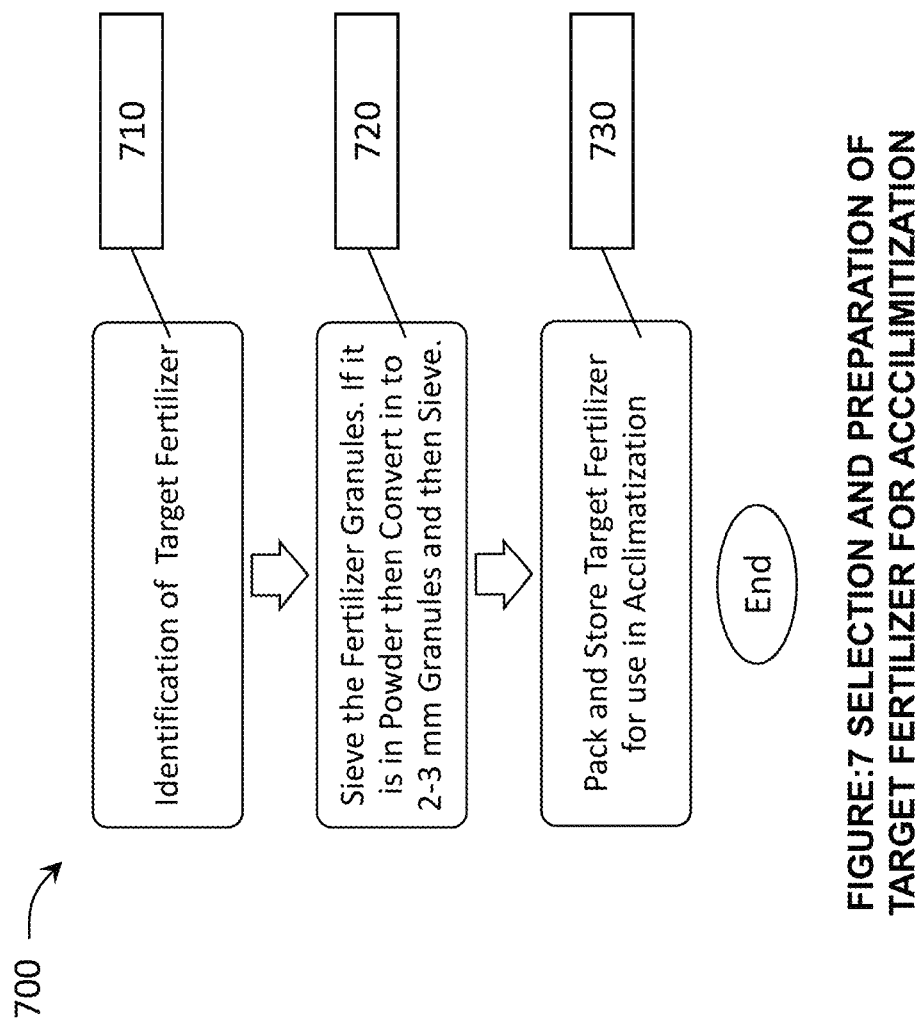
FIGURE:7 SELECTION AND PREPARATION OF TARGET FERTILIZER FOR ACCILIMITIZATION

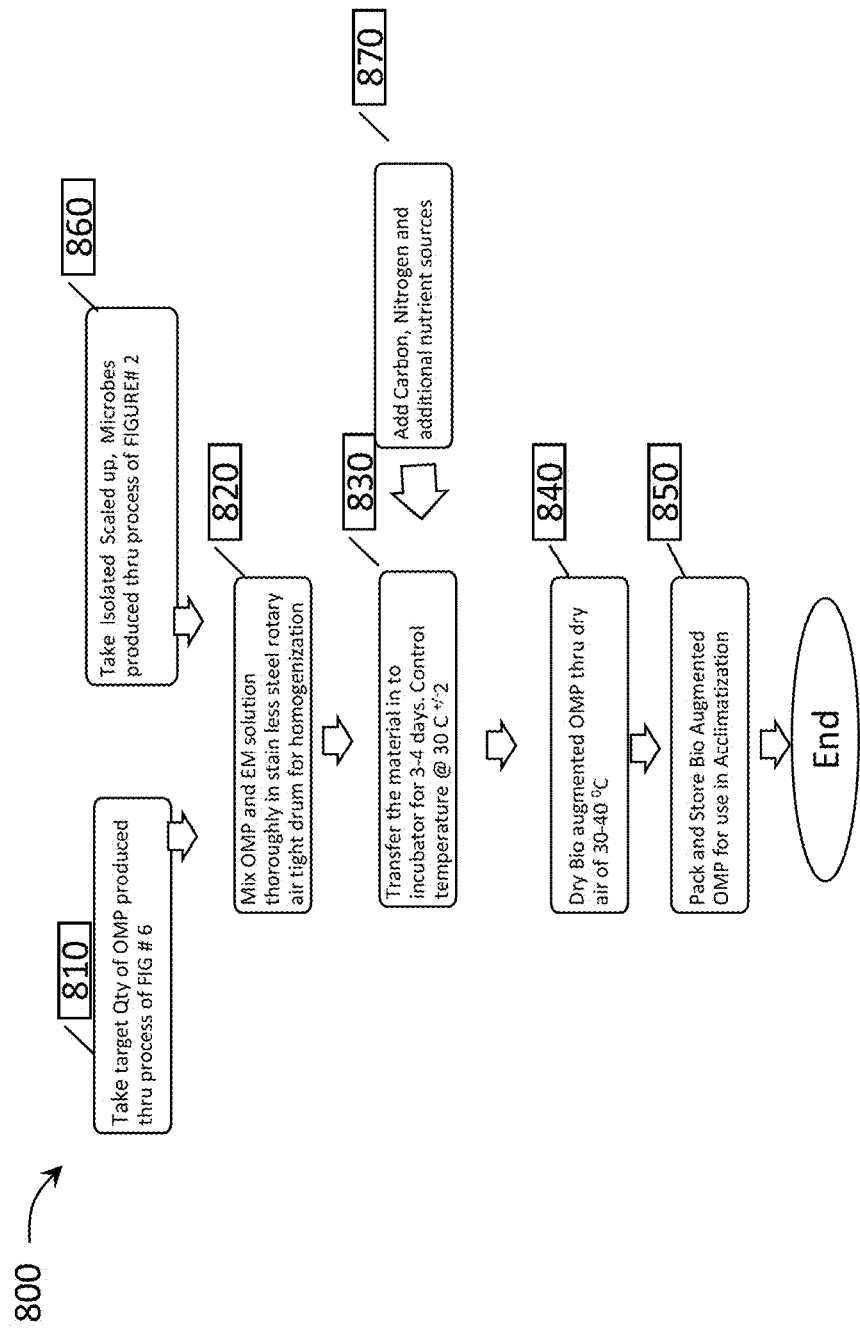
FIGURE:8 BIO AUGMENTATION OF OMP

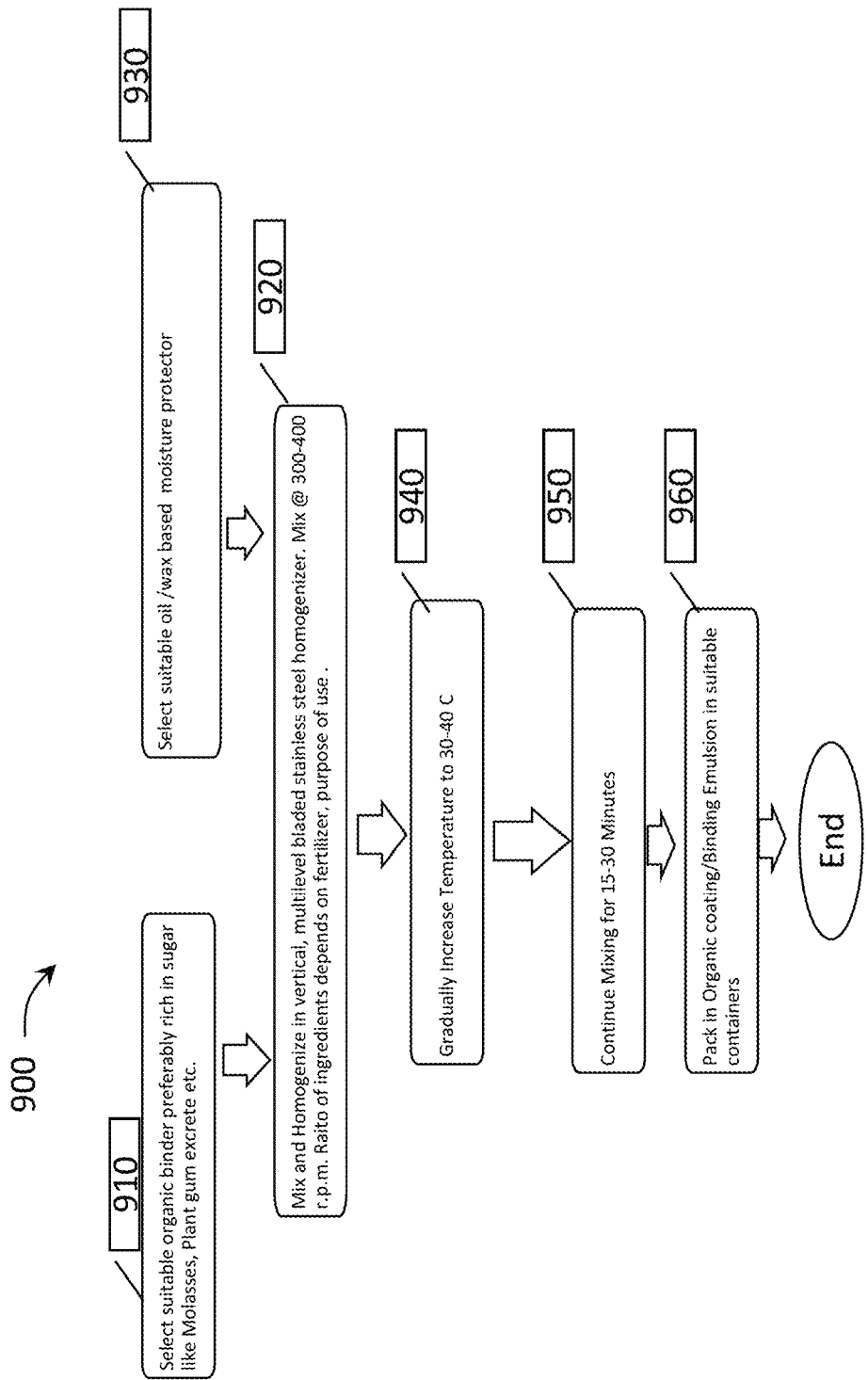
FIGURE:9 PREPRATION OF ORGANIC COATING/BINDING EMULSION

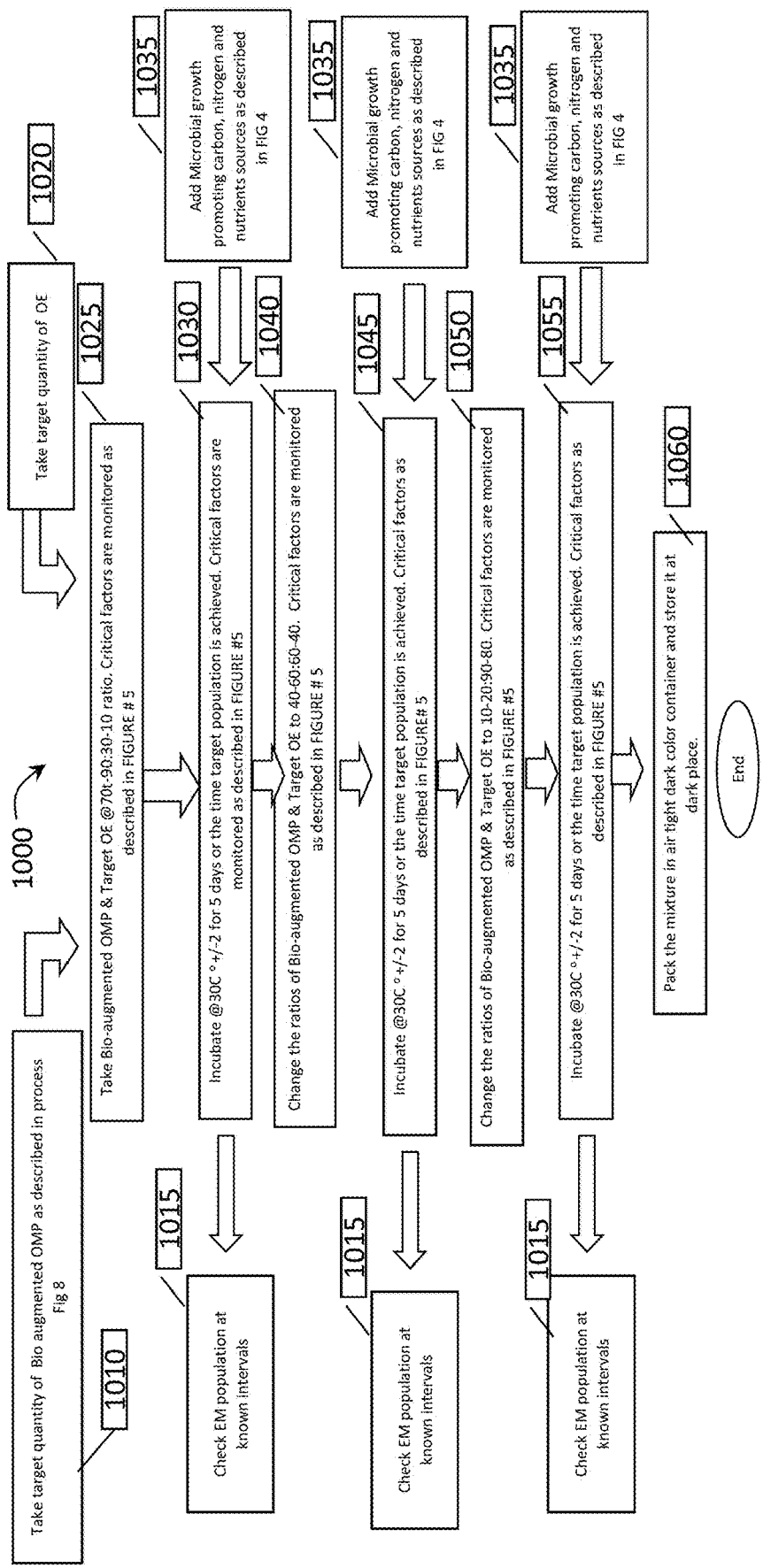
FIGURE:10 BIO AUGMENTED OMP EM INOCULATED ACCLIMATIZATION IN OE (SUGAR & OIL ETC COMPLEX EMULSION)

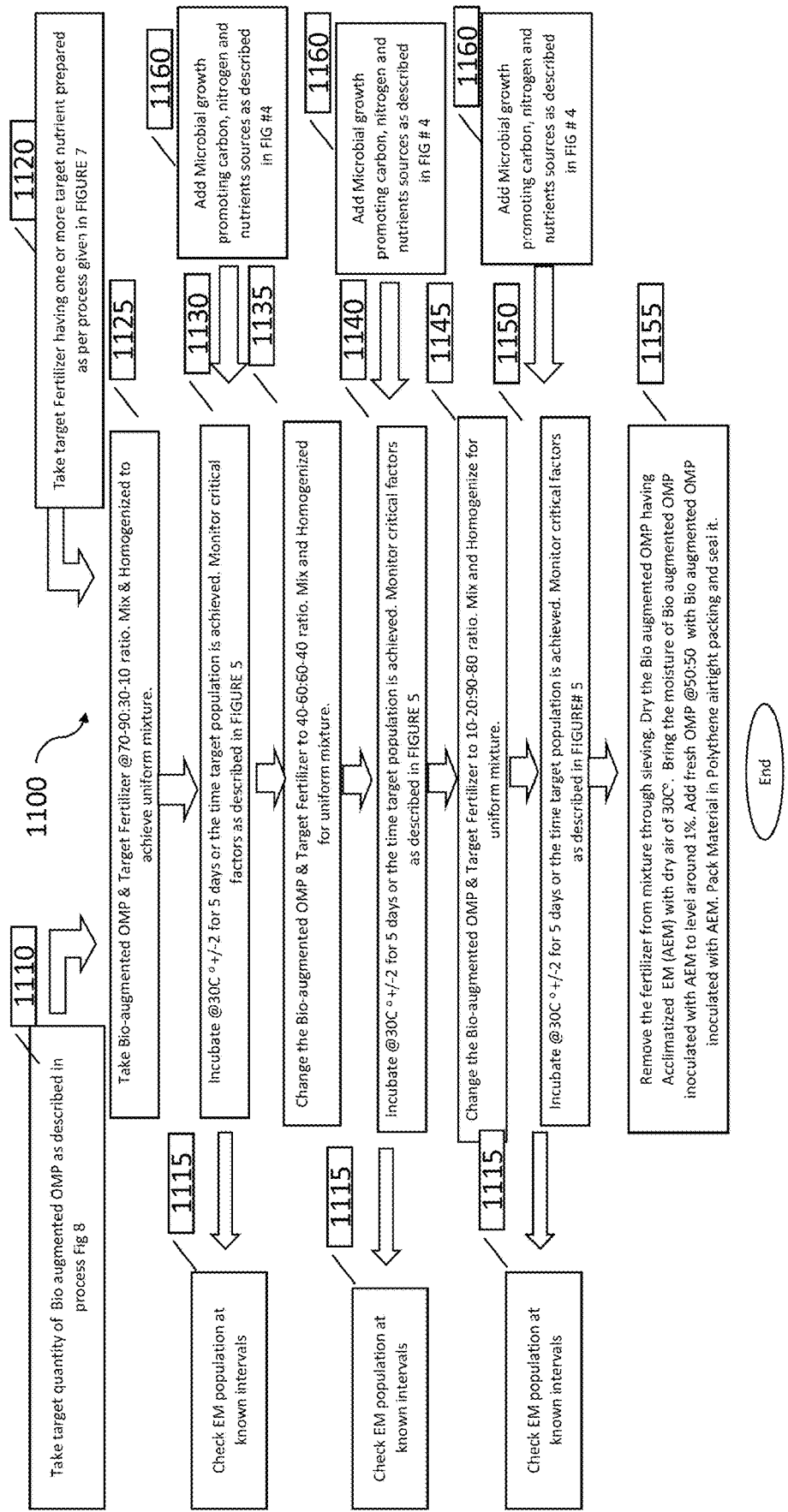
FIGURE:11 BIO AUGMENTED OMP HAVING ACCLIMATIZED EM

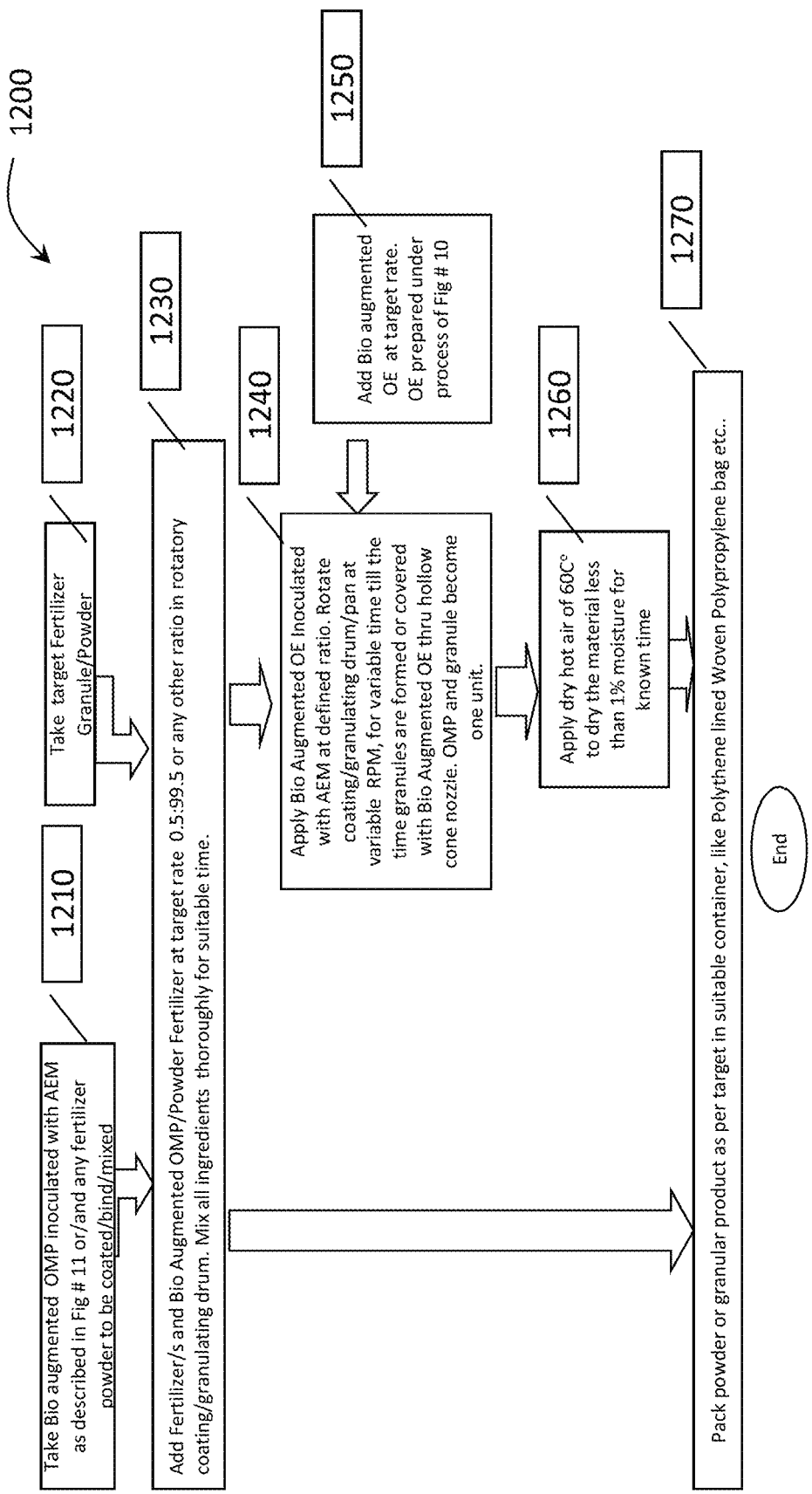
FIGURE:12 COATING/GRANULATION OF FERTILIZER WITH BIO AUGMENTED OMP & OE INNOCULATED WITH AEM AND /OR OTHER FERTILIZER Mixed and Granulated Fertilizer Externally Coated Fertilizer

CROSS SECTION OF DIFFERENT PRODUCTS

BIOAUGMENTED FERTILIZER WITH ACCLIMATIZED (PREFERABLY HALOTOLERANT) EFFECTIVE MICROORGANISMS AND METHODS FOR PRODUCING THE SAME

CROSS-REFERENCE TO RELATED APPLICATIONS

The present application claims priority to U.S. Provisional Patent Application No. 63/010,637, filed Apr. 15, 2020, the disclosure of which is hereby incorporated by reference in its entirety for all purposes.

RELATED APPLICATIONS

This application is related U.S. Pat. No. 8,932,382, 9,353,016, 9,617,190 and 9,994,494; U.S. patent application Ser. No. 15/971,513; Government of Pakistan Patent No. 142826, Bio Organo Phosphate (BOP), and Government of Pakistan Patent No. 142829, Bio-Active Nutrient Fortified Fertilizers (BNFF), which are hereby incorporated in their entirety by reference.

FIELD

This disclosure relates generally to the field of production of fertilizers based on the Integrated Plant Nutrient Management (IPNM) principles by improvement or enhancement of target fertilizer selected from simple chemical fertilizers; physically blended, coated, or complex chemical fertilizers; blend of organic and chemical fertilizers; or the like. Particularly, this disclosure relates to the field of isolation, screening, and acclimatization of one or more strains of plant nutrient mobilizing microorganisms, plant growth regulating microorganism, and other beneficial microorganisms, collectively referred to as effective microorganisms (EM), preferably halo tolerant microorganism that can remain active in high concentration salts of chemical fertilizers; and organic emulsion (OE) comprising of sugar, wax, oil, or the like used for binding and coating.

More particularly this disclosure relates to Bioaugmented fertilizer act as Integrated Plant Nutrient Management (IPNM) by assembling classical fertilizer; organic matter; and acclimatized (preferably (preferably halotolerant)) effective microorganism(s) (AEM) on or in one granule or particle coated with organic emulsion (OE) for sustainable, efficient plant nutrient management and environment-friendly impact on soil, wherein OE coating influences the shelf life of fertilizer in terms of biological, physical, or chemical properties of the fertilizer and coating of other nutrient components on the carrier fertilizer increases bio-availability of fertilizer nutrients and improves plant growth.

BACKGROUND

The background includes information that may be useful in understanding the present disclosure. It is not an admission that any of the information provided herein is prior art or relevant to the presently claimed invention, or that any publication specifically or implicitly referenced is prior art.

The existing approaches of plant nutrient management suffers from one or more of limitation such as sub-optimal use of immobile or less mobile nutrients.

I. The Problem with Sub-Optimal Use of Phosphatic Fertilizers:

Phosphorus (P) is an important nutrient required for plant growth and development, making up 0.2% of plants on a dry weight basis (Vance, 2001; Sachachtman, et al., 1998). It is a significant part of a plant's physiological and biochemical activities, such as photosynthesis, carbon metabolism, membrane formation, energy generation, nucleic acid synthesis, glycolysis, respiration, enzyme activation/inactivation, and nitrogen fixation (Bucio, et al., 2003).

Plants absorb most of their phosphorus as a primary orthophosphate ion (H2PO4)2 and a smaller amount from the secondary orthophosphate ion (HP04)2-. Plants also absorb certain soluble organic phosphates (i.e., PO4)3- in nucleic acid and phytic acid) (Sekhar and Aery, 2001; Mullins, 2009).

Among other advantages, the addition of phosphorus enables the plant to produce deeper and more abundant roots (Gupta and Sen, 2012). Conversely, a phosphorus deficiency alters root architecture, which ultimately affects seed development and normal crop maturity. (Williamson, et al., 2001). Thus, the availability of adequate phosphorus is fundamental to stimulate early plant growth and hasten maturity.

However, phosphorus is among the least bio-available nutrients in the soil (Takahashi and Anwar, 2007). While the total amount of phosphorus is 0.05% of soil content on average, only 0.1% of that amount is available to plants (Zou, et al., 1992). Even in fertile soils, less than 10 µM is available at pH 6.5, where it is the most soluble (Gyaneshwar, et al., 1998).

Soil phosphorus is found in both organic and mineral pools. Twenty percent (20%) to eighty percent (80%) of soil phosphorus is found in an organic form, such as phytic acid, while the rest of phosphorus is found as an inorganic fraction (Sachachtman, et al., 1998). As most arid and semi-arid soils regimes are deficient in phosphorus, phosphatic fertilizers are required to replenish the phosphorus demanded by crop plants.

However, more than 80% of the phosphorus applied as fertilizer stagnates in an immobile pool due to the presence of iron (Fe) and aluminum (Al) in acidic soils, and calcium (Ca) in neutral and alkaline soils, resulting in in-solubilization, precipitation, and adsorption or conversion into an organic form through biological activities (Harris, et al., 2006). This "fixation" of externally supplied phosphorus is common in alkaline and calcareous soils because of the higher activity of the calcium. Moreover, the application of externally supplied phosphorus favors the precipitation of relatively insoluble di-calcium phosphate and other basic calcium phosphates, such as hydroxyl-apatite and carbonate-apatite, decreasing the overall activity of phosphorus. Research suggests that phosphorus "fixation" in alkaline soils is largely attributed to its retention by clay saturated with calcium. This is because, calcium ions can retain a greater amount of phosphorus than those saturated with sodium or other monovalent ions. The formation of clay (Ca2+H2PO42-) is believed to be the most likely culprit.

Low availability of phosphorus to crop plants is a worldwide problem and thus crop yield on 30 to 40% of the world's arable land is limited by phosphorus availability (Vance, et al., 2003).

To overcome the consistent deficiency of phosphorus in alkaline/calcareous soils, soluble phosphatic fertilizers are applied to agricultural fields to maximize crop production (Shenoy and Kalagudi, 2005). Commercial fertilizers have played a very significant role in enhancing the per acre yield of crops and in return feeding the rising population of the world.

However, unfortunately the current production of phosphorus fertilizers is insufficient to meet rising demands. The alarming depletion of world resources of rock phosphate, along with their low use efficiency, has resulted in consistently increasing prices of phosphorus fertilizers. Elevated fertilizer prices, scarcity at the right time of application, as well as, sub-optimal doses largely account for low phosphorus fertilizers use (Alam, et al., 2005). In addition, the fixation/precipitation/adsorption/transformation of phosphorus decreases the efficiency of the applied chemical phosphorus fertilizers. Such sub-optimal use of phosphate fertilizers has led to the exogenous application of substantial quantities of phosphatic fertilizers to agricultural fields (Vassilev and Vassileva, 2003; Aziz, et al., 2006).

Accordingly, improved supply of organic phosphate, which not only supplies soluble organic phosphates but also releases a substantial amount of phosphorus through microbes by mineralization of organically bound phosphorus, would be highly desirable.

II. Current Limitations with Production of Fertilizers and Inefficient Use:

Rock phosphate (RP) is a basic raw material used for manufacturing of chemical phosphatic fertilizer. Globally, there are four major types of phosphate resources in the world, including marine, igneous, metamorphic, and biogenic phosphate deposits, which contain either of the fluorapatite (Cal o(PO4)6F2), hydroxyapatite (Ca1o(PO4)6(OH) 2), carbonate-hydroxy-apatite (Ca1O(PO4CO3)6(OH)z), francolite, dahllite, and collophane compounds (Straaten, 2002). Reserves are primarily found in Northern Africa, China, the Middle East, United States, Brazil, Canada, Finland, Russia, and South Africa. Large phosphate resources have also been identified on the continental shelves and on seamounts in the Atlantic and the Pacific Oceans. The world rock phosphate reserves are more than 300 billion tons, while annual consumption in 2011 was 191 million tons, up by 20% from 2010.

The desired grade of rock phosphate for manufacturing classic chemical fertilizers is the one having 30% P2O5 or higher, with low silica, magnesium, and other elements. However, the reserves of these grades are declining. A number of physic-chemical processes are employed to improve P205 content of low-grade rock phosphate and to remove undesired elements. Physical and thermal up-gradation of rock phosphate is achieved through crushing and screening, scrubbing, de-sliming, flotation, and magnetic and gravitation separation. However, a substantial amount of energy is consumed, and environmental pollutants are released in these processes.

Rock phosphate shows a considerable proportion of isomorphic substitution in the crystal lattice and has a variable proportion and amount of accessory minerals and impurities. Research shows that rock phosphates are appropriate for direct use in acidic soils for the supply of available phosphorus, but are unsuitable for neutral to alkaline soils (Sekhar and Aery, 2001). Thus, the release of bioavailable phosphorus from insoluble phosphates in alkaline/calcareous soil is important for sustainable agriculture by mobilizing it through a variety of advanced approaches where an inert phosphorus source is predictable and can be rehabilitated into plant available form (Kennedy and Smith, 1995; Caravaca, et al., 2004).

In addition to the phosphorous problem, the depleted organic matter reserves of alkaline/calcareous soils further decrease crop production, as well as affect numerous soil metabolic processes (Mullins, 2009). Most organic matter decomposes quickly when applied in a hot and climate, which explains why the soils are poor in organic matter. However, organic matter is a universal remedy and is known to improve soil health and nutrients availability to plants. Most organic wastes area potential sources of plant macronutrients, as well as, a large amount of micronutrients. However, it is difficult to increase the organic matter content of soils that are well aerated, such as in coarse sands and soils in warm-hot regions because the added materials decompose rapidly (Hamza and Anderson, 2010).

Generally, warm climate tends to enhance the microbial decomposition of organic matter. Normally, soils are low in organic carbon. When microorganisms are inoculated to such soils, their population typically do not reach a level at which they can perform efficiently. In many cases, they do not survive for long, often resulting in inconsistent performance. This situation alarmingly needs restoration of organic matter through an exogenous application. But unlike chemical fertilizers, these organic amendments do not provide enough nutrients, particularly phosphorus. Therefore, after the introduction of chemical fertilizers and high yielding varieties in the cropping system, farmers are largely dependent on continuous injection of chemical fertilizers to meet the high plant nutrient requirements.

Nevertheless, the use of organic waste and chemical fertilizers not only requires constant replenishment (needing significant resources to create), but they are also a source of pollution, requiring additional management for short term and long-term environmental impacts. Organic waste management is a major environmental issue because constant population growth means commensurately more waste to be recycled. Likewise, chemical fertilizer manufacturing is known to generate a wide range of air emissions, hazardous materials, effluents, wastewater, and other harmful byproducts (e.g., hydrofluoric acid, silicon, tetrafluoride, fluoride, SO4 phospho-gypsum, NH4, NO, fluoride air, P2O5 effluents, dust fluoride effluents, chloride, cadmium, lead, radionuclides, and sulfur compounds, etc.). Further, chemical fertilizer manufacturing also consumes substantial energy, ranging from 120 to 450 KWh per ton of P205, depending on the process employed. Moreover, chemical fertilizer manufacturing consumes substantial amounts of water, ranging from 2 to 150 cubic meters per ton of P2O5 (UNEP Technical report, 1996; World Bank Group report, 2007).

As the world population grows, and the need for agricultural farming using organic waste and chemical fertilizers increases, recycling organic wastes is becoming a major environmental issue. Composting organic residues would be the best possible means to recycle. The use of composted products improves soil properties, and in turn improves soil productivity, thus promoting the plant growth (Vassilev and Vassileva, 2003).

Thus, the efficient use of organic fertilizers is a key strategy not only for improving soil organic matter content and nutrients supply, but also for reducing the input cost of mineral fertilizers and promoting a healthier environment (Bhattacharyya, et al., 2007; Ahmad, et al., 2007a).

Organic approaches that partially supplement nutrients through organic sources (and which do not involve synthetic formulation) have gained considerable response during recent years. However, under the current hegemony of organic fertilizer practitioners and accelerated decomposition, the use of organic materials remains poor in nutrient content and do not completely fulfill the nutritional needs of crops, particularly phosphorus, for normal growth and yields (Ahmad, et al., 2007b).

Laboratory research suggests that organic fertilizers can be used as rich carriers of plant growth promoting rhizobacteria. These not only mobilize nutrients in soils but also facilitate the uptake of less mobile nutrients, such as phosphorous, by altering root architecture. These synergistic effects benefit crops tremendously (Shahroona, et al., 2008). Moreover, novel plant growth promoting rhizobacteria (PGPR) isolates show promising attributes when developed and used as bio-fertilizers to enhance soil fertility and promote plant growth (Dastgeer, 2010).

However, an important issue in the use of PGPR isolates is the ability to consistently deliver the "right type" of bacteria that plays an appropriate role in phosphorus nutrition. Unless the "right type" of bacteria is delivered to solubilize/mineralize the organic matter in soils, phosphorous availability to plants cannot be enhanced (Ahmad, et al., 2009; Walpola and Yoon, 2012).

Based in part on the hegemony of current organic fertilizer users and based on sparse research available on cultivating PGPR isolates, let alone those that are augmented with phosphate solubilizing microorganisms (PSM) or plant growth regulating microorganisms (PGRM) including, but not restricted to, prokaryotes such as algae, bacteria, protozoa, etc., and eukaryotes such as fungi, etc.; there exists a void in the industry as to the large scale production of bio-organo-phosphate (BOP) fertilizer using these technologies.

Accordingly, improved efficacy due to less probability of fixation, precipitation, or in-solubilization than current commercial soluble chemical/inorganic fertilizers is desired. In addition, the environmentally conscious production, application, and management of organic fertilizers are likewise desirable. To sum up, there exists a long-felt industry need for the large-scale production of bio-organo-phosphate (BOP) fertilizer that consistently and optimally delivers phosphorous to plants to help improve root architecture, enhance nutrient uptake, accelerate healthy growth, and hasten maturity.

III. Bioavailability of Immobile/Less Mobile Nutrient Elements:

Agriculture has been providing food and shelter to global populations since long. Land use for agriculture is 38% of 13 billion hectares worldwide with 2.9% contribution to global GDP. According to the 2020 projections, agriculture will be challenged to supply an increasing population, especially in developing countries. Fertilizers that contain both macro and micronutrients are considered the most important input for sustainable crop production with an approximate increase of 25% in yield and productivity through their use. Both macro and micronutrients play a critical role in overall agricultural productivity enhancement. Macronutrients of immobile/less mobile elements, such as phosphorus, and the majority of such micronutrients including, but not limited to, zinc, iron, boron, and manganese, are increasingly becoming a limiting factor in obtaining optimum crop production. It has been found that deficiency of some macro and micronutrients affects the ability of plants to effectively uptake and use other mobile and immobile nutrients present in the soil. In particular, zinc deficiency has recently been reported in a variety of crops. Zinc is also critical for human health. Its deficiency in humans may lead to compromised immunity, hair loss, skin lesions, loss of appetite, diarrhea, loss of taste and smell, and many other disorders. It is widely accepted that the best source of micronutrients to humans is through agricultural products. Therefore, micronutrient fortified crops, such as zinc-fortified crops, are an excellent source of nutritional balance for human beings.

Immobile/less mobile macro and micronutrients are taken up by plants continuously from emergence to maturity. A variety of products containing these nutrients are available in the market. However, the application methods to target crops do not support sufficient availability of these nutrients to fulfill the plants' requirements throughout the entire growth cycle. For instance, the uptake of zinc by crops is very low compared to the quantity applied. More than 90% of the applied zinc remains in non-available forms in the soil. Particularly in alkaline soil, it results in financial losses to farmers in the form of lower yields due to nutrient deficiency. It has been documented that only 4-8% of the applied zinc is utilized by the target crop in alkaline soils. Zinc deficiency also affects the plant's efficient use of other mobile and immobile/less mobile elements, even though these elements are sufficiently available in the soil. Thus, it affects agricultural productivity and the cost-benefit ratio of all nutrients for farmers.

A wide variety of commercial fertilizer products containing immobile/less mobile nutrient elements is available in the market. However, these fertilizers either have low efficacy or are not suitable for all types of crops and soils. For instance, phosphorus use efficiency is around 20-25% and zinc use efficiency ranges between 4-8%. In addition, market availability of products including zinc and other micronutrients in a form readily available to crops is yet another crucial factor that is seriously affecting farmers' ability to enhance productivity.

Accordingly, there is a need to develop an effective fertilizer to enhance bioavailability of immobile/less mobile macro and micronutrients in order to reduce losses and improve agricultural productivity.

IV. Integrated Plant Nutrient Management (IPNM):

The International Fertilizer Association reported that three countries with the highest fertilizer use in 2006 were China, India, and USA consuming 50.15, 21.65 and 20.83 million tons of NPK fertilizers respectively, compared with consumption in 1961 of 1.01, 0.42 and 7.88 million tons respectively (htpp://www.fertilizer.org/ifa). The challenge, therefore, is to continue agricultural productivity in a way that minimizes the harmful environmental effects of fertilizers. The effort of the scientific community is to maximize the plant use of applied fertilizers by inventing products and techniques through integrated plant nutrient management (IPNM) system. Inventing new fertilizer production technologies with minimum or lowest possible harmful emissions would, off course, be an important contributing factor.

Three main components of IPNM system as defined by Food and Agriculture Organization (FAO), 1998 are:
1. Maintain or enhance soil productivity through a balanced use of fertilizers combined with organic and biological sources of plant nutrients;
2. Improve the stock of plant nutrients in the soils; and
3. Improve the efficiency of plant nutrients, thus, limiting losses to the environment (FAO Rome 1998)

Plants require all food nutrients in variable proportion right from germination to termination.

L Lujin et.al 2004 reported balanced fertilizer addition of K increased garlic crop leaf yield by 121-156% and clove yield 45 to 71% vs control (zero K). at Shuikou, China. (Better crops Vol. 88 (2004, No. 4).

Nobel R. Usherwood and Wiilam I. Segars 2001 conducted a long term (10 years) trial and observed that in a balance use of NPK vs N alone, the variance in yield was 648 lb. grains/acre in the first year, while at the tenth year it increased to 5,840 lb. grains/acre.

Chemical fertilizers and Biofertilizers combined with the organic fertilizers enrichment of plant, favors the physical and biological properties and increase elements use potential of the plants that results in remarkably healthy and high-quality production (Tandon, 1992).

The integrated nutrient management favorably affects the physical, chemical and biological properties of soils. Integrated nutrient supply involves a conjunctive use of fertilizers and organic sources of nutrients (Roy, 1992).

V. Effect of Microbe on Plant Nutrient Supply & Yield:

The role of microorganisms in making plant nutrient available is pivotal. Microbial inoculation and a lower dose of fertilizer (75% of Nitrogen alone and Phosphorus alone) produced Beet root tuber of 302 gm/plant vs 215 gm/plant of alone Nitrogen (N) and Phosphorus (P) as reported by J. Ajay Kumal et al. 2013.

Microorganisms population in soil per gram for Bacteria $10^8$-$10^9$, Actinomycetes $10^7$-$10^8$, Fungi $10^5$-$10^6$, Algae $10^4$-$10^5$, Protozoa $10^3$-$10^4$, Nematodes $10^2$-$10^3$ has been reported by Hoorman and Islam—Ohio State University (2010).

Similarly, nutrient uptake in treatment with microbial inoculation and NP at 75% dose, was 135.14, 28.96 and 49.04 kg/ha of N, P, and Potassium (K) respectively vs the treatment where NP were applied @100% i.e. 106.41, 22.85 and 39.12 kg/ha N, P, and K respectively (Kumar et al. 2014).

Synergistic use of biochar, compost and plant growth-promoting rhizobacteri for enhancing cucumber growth under water deficit conditions caused significant increase in the shoot length, shoot biomass, root length and root biomass, which were respectively 88,77,89, and 79% more than the un-inoculated control (Nadeem et al. 2017).

Apple root inoculation with PGPR strains increased P, K, Iron (Fe), Manganese (Mn) and Zn concentration. The main reason of this was the organic acids build-up by bacteria in the plant rhizosphere which decreased the rhizospheric soil pH and improved the accessibility of these elements (Karlidiag et.al. 2007).

The low efficiency of plants in the uptake of fertilizers is a major factor that aggravates negative environmental effects (Barlog and Grzebisz, 2004). Over 50% of the applied N is lost from the agricultural system as N2 gas, trace gases or leached nitrate (Vitousek et al. 1997: Tilman 1998).

The same emphasizes need of improving uptake efficiency of plants with the help of microbes.

VI. Effect of Environmental Stress like Soil Salinity:

Tripathi et.al (2006) reported that average electrical conductivity (EC) during summer season was about five times higher than that during the monsoon season. The average microbial biomass C (MBC), average basal soil respiration (BSR), and average fluorescein di-acetate hydrolyzing activity (FDHA) were the lowest during the summer season, indicating a negative influence of soil salinity. About 59%, 50% and 20% variation in MBC/OC, FDHA/OC and BSR/MBC (metabolic quotient, qCO2), respectively, which are indicators of environmental stress, could be explained by the variation in EC.

Wichern et al. (2006) reported that biological indices like soil respiration and microbial biomass decreased with increasing levels of salinity, underlying the detrimental effect of salinity on soil microorganisms. This effect was reduced after the addition of maize straw, documenting the importance of organic matter amendment in counteracting the negative effect of salinity on microbial communities and related mineralization processes.

Accordingly, there is a dire need to control soil salinity that can improve activity of microorganisms for effective nutrient management.

VII. Coating of Fertilizers:

A wide variety of commercial chemical fertilizers containing single and multiple nutrients are available in the market. The chemical/storage compatibility of different plant food nutrient supplementing chemical fertilizers limits the mixing/solving/blending ability of the desired plant food nutrients. For instance, the difficulty in chemical blending of water-soluble Zinc (Zn) in water-soluble chemical fertilizer Di-Ammonium Phosphate due to the antagonistic effect of both. Hence there is a need to develop a coating material, which can bind multiple nutrients without having a chemical reaction. This physical binding will ease the farmer to apply multiple nutrients simultaneously without additional cost and effort. However, the coverage of micronutrient will be more if loaded on primary nutrient as a greater quantity of macronutrient is required than the micronutrient. Such physical coating will expand the range of nutrient loaded in one prill/granule and also improve performance. It is mandatory for all prill or granule or crystalline fertilizer manufacturer that the products remain free flowing during storage according to Pakistan Standards (for Urea, Calcium Ammonium Nitrate, Di-ammonium Phosphate, Mono Ammonium Phosphate etc.), European Union, and Indian Fertilizer Standards.

A variety of chemical compounds are used. Phosphoric ester and fatty tri-alkyl-amine compound reported as anti-caking agent is a new invention (Martinex et al. 2015 U.S. Pat. No. 8,932,490B2-2015).

A cationic aliphatic amine, a carboxylic acid, and a small amount of alkali also act as an anticaking agent (Habasko et al. 1975 U.S. Pat. No. 3,926,841).

Spraying of 30-70% solution of an aliphatic primary amine, example fatty amine in mineral oil on to the agitated particulate material. This is a method disclosed in U.S. Pat. No. 3,186,828.

U.S. Pat. No. 3,305,491 describes how to prevent caking of fertilizer and salts by adding of cation surface-active composition comprising an acid mixture of cationic fatty amines and fatty acids.

According to U.S. Pat. Nos. 3,234,003, 3,3234,006, and 3,250,607, a conditioning agent is known in the form of a powder, which is obtained by coating microscopic particle of certain clay with a small amount of solution of a hydrophobic aliphatic amine in mineral oil. The coated clay product thus obtained is dusted on the surface of the fertilizers granules or prills.

These approaches remain ineffective and hence there is a need to provide the fertilizer coating agent considering applied chemical properties of the target fertilizer. Since chemical fertilizers are applied to the soil, which has its own micro flora.

There are variety of microorganism containing products available in the market. These products are in liquid and solid forms, but all are applied in isolation or blended with fertilizers. The performance of such products is usually inconsistent due to:

1. Traditional microbial products are isolated from nature, multiplied in ideal conditions and are packed in carbon-rich medium. These strains remain viable in carbon-rich, ideal conditions but their viability reduces when they are packed/blended in a high salt carrier.
2. Usually, the farmer uses fertilizers and microbial products in isolation. Even if they are physically blended with chemical fertilizers, both the products (fertilizers and bio-fertilizers) get separated due to lack of binding. Chances of microorganisms and fertilizer granule interaction are unpredictable. Secondly, if the microorganisms and fertilizers have interaction, then the capability of microbial strains to work under high salt levels is another challenge.

3. The currently known art of fertilizer coating material focuses mainly on two areas, i.e., the physical properties of granule (stability, free flow ability) and chemical efficiency of fertilizers (reduced/controlled release/transformation of fertilizers or controlled release of nutrients). There is no focus on developing a coating material that serves the purpose of INPM along with improvement in physical and chemical performance.

Foregoing emphasizes a need to provide a population of microorganism, preferably halo tolerant microorganism that can have ability to mobilize nutrients from soil and/or regulate plant growth. There is also a need to improve the capacity of microbial strains to remain active under high salt levels and other stress condition. Performance targeted high salt concentration regime for example fertilizer in particle/granule form for application to soil in solid form, preferably at low carbon level is required. It is also important to develop an organic binding solution, which can be used for binding/coating effective microorganisms and other organic/inorganic materials on a carrier fertilizer. In addition to coating material, this organic binder should provide energy and protective layer to maintain the target microorganism population on carrier fertilizers which can preferably enhance productivity in the field. The coating material should be robust enough to improve the physical and chemical properties of target fertilizer simultaneously. Thus, there exists need for an overall approach for improvement or enhancement of target fertilizer by incorporation or coating of acclimatized effective microorganism along with organic matter to provide an integrated plant nutrient management (IPNM) fertilizer product for sustainable and efficient plant nutrient management.

SUMMARY

In a general aspect the present disclosure provides a method to convert classical fertilizer, an organic or inorganic fertilizer to bioaugmented fertilizer product (serve as INPM) by assembling: one or more of mineral nutrient, organic matter and microorganisms on or in one granule or particle for sustainable, efficient plant nutrient bioavailability and environment-friendly impact on soil.

More particularly this disclosure relates to Bioaugmented fertilizer with acclimatized (preferably halotolerant) effective microorganism(s) (AEM) comprising of, target or carrier fertilizer; organic elements in the form of organic matter prepared (OMP) bioaugmented with AEM; optionally organic emulsion (OE) bioaugmented with AEM; and fertilizer specific AEM consortium.

In one aspect there is provided a method of producing a bioaugmented fertilizer with acclimatized (preferably halotolerant) effective microorganism (AEM) comprising the steps of:
providing a bioaugmented organic material preparation (OMP) inoculated with an acclimatized (preferably halotolerant) effective microorganism (EM);
providing a bio-augmented organic emulsion (OE) inoculated with AEM; and
blending the bio-augmented organic material preparation (OMP) inoculated with AEM, with a target fertilizer; and coating with the bio-augmented organic emulsion (OE) inoculated with AEM to provide bioaugmented fertilizer with AEM.

In one specific aspect there is provided a method of producing a bioaugmented fertilizer with acclimatized (preferably halotolerant) effective microorganism (AEM) comprising the steps of:
providing a culture of (preferably halotolerant) effective microorganisms by:
isolating (preferably halotolerant) microorganisms preferably from salt affected soils;
screening and selecting (preferably halotolerant) nutrient mobilizing microorganisms (NMM) and (halotolerant) plant growth regulating microorganisms (PGRM);
culturing selected NMM and PGRM separately; and
mixing cultures of NMM and PGRM to provide a culture of (preferably halotolerant) effective microorganisms EM;
preparing a bio-augmented organic material preparation (OMP) by:
providing Organic matter prepared (OMP);
inoculating the OMP with the (preferably halotolerant) effective microorganisms EM culture; and
incubating the OMP with the EM under suitable condition and at defined period to provide a bioaugmented OMP;
preparing organic emulsion (OE);
providing a bioaugmented organic material preparation (OMP) inoculated with an acclimatized (preferably halotolerant) effective microorganism (AEM) by;
inoculating the bioaugmented OMP in a high salt concentration fertilizer or in a sugar-based OE in defined ratio in stepwise manner with increasing concentration and incubating under suitable condition and for a period sufficient to provide bio-augmented OMP inoculated with acclimatized EM;
blending the bio-augmented OMP inoculated with AEM, with a target fertilizer and binding, coating or granulating the target fertilizer with the bio-augmented OMP inoculated with AEM to provide bioaugmented fertilizer with AEM.

In another aspect, the method further comprises coating the bioaugmented fertilizer with AEM, by applying another fertilizer and carrying out coating or granulation to provide powder or granular fertilizer product.

In yet another aspect, the method further comprises coating the bioaugmented fertilizer with AEM, by applying a bio-augmented organic emulsion (OE) inoculated with AEM to provide coated fertilizer product.

In an exemplary aspect, there is provided a culture of (preferably halotolerant) effective microorganisms comprising the steps of:
isolating (preferably halotolerant) microorganisms preferably from salt affected soils;
screening and selecting effective (preferably halotolerant) nutrient mobilizing microorganisms (NMM) capable of improving the bioavailability of immobile or less mobile or mobile plant nutrients to the plant;
screening and selecting effective (preferably halotolerant) plant growth regulating microorganisms (PGRM) capable of regulating plant growth;
growing selected NMM and PGRM separately; and
optionally mixing cultures of NMM and PGRM and providing a culture of (preferably halotolerant) effective microorganisms EM.

In an exemplary aspect, the step of providing the bio-augmented organic material preparation (OMP) comprises:
providing Organic matter prepared (OMP);

inoculating the OMP with the (preferably halotolerant) effective microorganisms EM culture; and incubating the OMP with the EM under suitable condition and at defined period to provide a bioaugmented OMP.

In an exemplary aspect the Organic matter prepared (OMP) is prepared by the process comprising:

selecting suitable organic matter for example plant or animal solid waste, humic acid or the like;

drying the organic matter and separating any undesired material; and converting the dried organic matter to 300-400 mesh by grinding at a temperature not exceeding 30-40° C.

In an exemplary aspect, the step of providing the bio-augmented organic material preparation (OMP) inoculated with AEM comprises:

inoculating the OMP with the (preferably halotolerant) effective microorganisms EM culture to provide a bioaugmented OMP;

incubating the culture comprising the EM and OMP, with a high salt concentration fertilizer to acclimatize the EM;

screening, isolating and cultivating the acclimatized EM (AEM); and inoculating the AEM bio-augmented organic material preparation (OMP) inoculated with and storing in OMP.

In an exemplary aspect, the step of providing an oil emulsion (OE) for coating and or binding comprises:

selecting an organic binder rich in sugar as an aqueous phase;

selecting an oil or wax based moisture protector as an oil phase; and mixing the aqueous phase and the oil phase and emulsifying by homogenizing the mixture in a suitable equipment, at a suitable mixing speed and condition, for a period sufficient to provide the OE.

In an exemplary aspect, the step of providing a bioaugmented oil emulsion (OE) inoculated with AEM comprises the steps of:

preparing an organic emulsion (OE) of a sugar based organic binder with an oil or wax based moisture protectant;

inoculating OE with (preferably halotolerant) effective microorganisms EM culture to provide a bioaugmented OE;

gradually changing the ratio of OE and EM to desired target OE concentration for achieving acclimatized EM (AEM);

isolating the AEM after achieving target acclimatization level; and providing the bio-augmented organic emulsion (OE) inoculated with AEM cultivating the acclimatized AEM and storing in OE.

In an aspect the bio-augmented OE inoculated with AEM is used for binding/coating of bio-augmented OMP inoculated with AEM. The bio-augmented OE inoculated with AEM is used in specific dose for properly binding/coating of bio-augmented OMP inoculated with AEM for different types of target fertilizer for example ranging between 0.1-20% of the coated material.

In an alternate exemplary aspect, there is provided an integrated process of bioaugmentation of organic matter prepared (OMP) and acclimatization of (preferably halotolerant) effective microorganisms (EM) in high concentration of oil emulsion (OE), the process comprises the steps of:

taking bioaugmented OMP and OE in defined ratio and incubating under suitable condition in presence of microbial growth promoting nutrients and for a period sufficient to acclimatize the EM comprised in the bioaugmented OMP;

changing step wise the ratio of bioaugmented OMP and OE sequentially by increasing the concentration of OE and in each step incubating the mixture under suitable condition in presence of microbial growth promoting nutrients and for a period sufficient to achieve desired level of acclimatization the EM population in OE.

Other compositions, variations, methods, features and advantages of the subject matter described herein will be or will become apparent upon examination of the following detailed description. It is intended that all such additional compositions, variations, methods, features, and advantages be included within this description, be within the scope of the subject matter described herein, and be protected by the accompanying claims. In no way should the features of the example embodiment be construed as limiting the appended claims, absent express recitation those features in the claim.

BRIEF DESCRIPTION OF THE FIGURES

The following drawings form part of the present specification and are included to further illustrate aspects of the present disclosure. A more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the disclosure. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 1 is an exemplary flowchart illustrating an exemplary overall process for production of Bioaugmented IPNM fertilizer with Acclimatized Effective (preferably halotolerant) Microorganisms (AEM).

FIG. 2 is an exemplary flowchart illustrating the process as per an exemplary embodiment for isolation and selection of effective (preferably halotolerant) microorganisms including nutrient mobilizing microorganisms and plant growth regulating microorganisms.

FIG. 3 is a recipe for medium for (preferably halotolerant) Effective Microorganisms cultivation (F1 Breeding)

FIG. 4 is an exemplary recipe for medium for (preferably halotolerant) Effective Microorganisms (AEM) cultivation at commercial scale.

FIG. 5 depicts exemplary critical factors for (preferably halotolerant) EM acclimatization.

FIG. 6 is an exemplary flowchart illustrating the process as per an exemplary embodiment for Organic matter prepared (OMP)

FIG. 7 is an exemplary flowchart illustrating the process as per an exemplary embodiment for selection and preparation of target fertilizer for acclimatization.

FIG. 8 is an exemplary flowchart illustrating the process as per an exemplary embodiment for bioaugmentation of OMP.

FIG. 9 is an exemplary flowchart illustrating the process as per an exemplary embodiment for preparation of Organic Emulsion (OE) for coating or binding.

FIG. 10 is an exemplary flowchart illustrating the process as per an exemplary embodiment for acclimatization of EM comprised in bioaugmented OMP in OE to provide bioaugmented OMP with AEM inoculated in OE.

FIG. 11 is an exemplary flowchart illustrating the process as per an exemplary embodiment for bioaugmented OMP inoculated with acclimatized (preferably halotolerant) effective microorganism (AEM), wherein the acclimatization is carried out in high salt fertilizer.

FIG. 12 is an exemplary flowchart illustrating the process as per an exemplary embodiment for fertilizer coating/granulation/mixing (if all products are powder) with bio-augmented OMP and OE inoculated with AEM and/or other fertilizer.

DETAILED DESCRIPTION

Figures 13A, 13B:
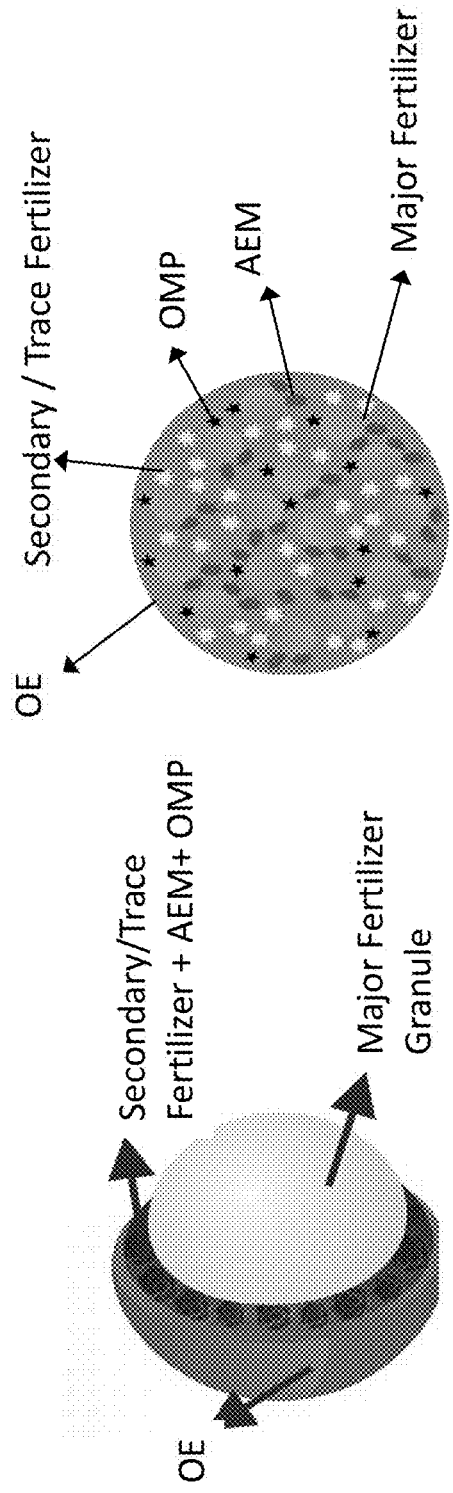
FIGS. 13A and 13B are exemplary cross sections/diagrams of different coated/granulated/mixed products bioaugmented with OMP and OE inoculated with AEM and/or other fertilizer.

The following description of the preferred embodiments of the disclosure is not intended to limit the disclosure to these preferred embodiments, but rather to enable any person skilled in the art to make and use this disclosure. Although any methods, materials, and devices similar or equivalent to those described herein can be used in the practice or testing of embodiments, the preferred methods, materials, and devices are now described.

The expressions "target fertilizer", "carrier fertilizer", "primary fertilizer", "classical fertilizer" and "base fertilizer" are used interchangeably and refers to the fertilizer which is used as base, or a carrier augmented by coating, binding, or incorporating of other components to provide the final fertilizer product.

The term "fertilizer" as used herein refers to simple chemical fertilizers, physically blended, coated, or complex chemical fertilizers, blend of organic and chemical fertilizers or the like.

Plant nutrients elements are categorized into mobile, less mobile and immobile nutrient elements in respect of bioavailability. Mobile elements are soluble in water and are distributed in soil by the flow of water through the soil. Immobile or less mobile nutrient elements are insoluble or partially soluble in water and are not freely distributed by the flow of water throughout the soil. Instead, immobile or less mobile nutrient elements move through soil by diffusion and are taken up by root contact. Some nutrient elements, when complex with specific organic compounds, are also referred to as less mobile. Similarly, if nutrient elements are converted into a state in which some fraction moves slowly with soil water are also called less mobile. Nutrient elements are referred to as immobile if they do not travel with soil water at all. The key task in plant nutrient management is to synchronize plant food nutrients bioavailability to plants in term of type, time and quantity so that maximum plant genetic potential can be realized.

Accordingly, this disclosure provides enhanced bioavailability of the target nutrient elements as IPNM product.

In some embodiments, there is provided a Bioaugmented Integrated Plant Nutrient Management (IPNM) fertilizer with acclimatized (preferably halotolerant) effective microorganism(s) (AEM) comprising of: target or carrier fertilizer; bioaugmented organic matter prepared (OMP) inoculated with AEM; with or without organic emulsion (OE) which may be bioaugmented with AEM; and fertilizer specific AEM consortium.

In some embodiments, the present disclosure relates to the improved process of acclimatizing effective nutrient mobilizing and plant growth regulating microorganisms jointly referred to as EM. This should be capable to remain effective in the presence of high salt carrier like fertilizers when mixed or coated in or on fertilizer in the presence or absence of organic emulsion (OE) for coating or binding of fertilizer. The use of fertilizer as the carrier may have a synergetic effect on plant nutrient bioavailability.

The use of OE may achieve a more stable product when, any organic or inorganic source of plant nutrient elements is physically coated or mixed on or in the fertilizer, or any organic or inorganic nutrient bioavailability improving material such as bio stimulants, Carbon, compost, humic acid or any other material with or without effective microorganism is physically coated or mixed on or in the fertilizer. The objective to use OE may include reduce fertilizer caking tendency and the disintegration of granules due to dryness or high moisture etc.

In some embodiments, there is provided a method of producing a bioaugmented fertilizer with acclimatized (preferably halotolerant) effective microorganism (AEM) comprising the steps of:
  providing a bioaugmented organic material preparation (OMP) inoculated with an acclimatized (preferably halotolerant) effective microorganism (EM);
  providing a bio-augmented organic emulsion (OE) inoculated with AEM; and
  blending the bio-augmented organic material preparation (OMP) inoculated with AEM, with a target fertilizer; and coating with the bio-augmented organic emulsion (OE) inoculated with AEM to provide bioaugmented fertilizer with AEM.

In some embodiments, there is provided a method of producing a bioaugmented fertilizer with acclimatized (preferably halotolerant) effective microorganism (AEM) comprising the steps of:
  providing a culture of (preferably halotolerant) effective microorganisms by:
    isolating (preferably halotolerant) microorganisms preferably from salt affected soils;
    screening and selecting (preferably halotolerant) nutrient mobilizing microorganisms (NMM) and (preferably halotolerant) plant growth regulating microorganisms (PGRM);
    culturing selected NMM and PGRM separately; and
    mixing cultures of NMM and PGRM to provide a culture of (preferably halotolerant) effective microorganisms EM;
  preparing a bio-augmented organic material preparation (OMP) by:
    providing Organic matter prepared (OMP);
    inoculating the OMP with the (preferably halotolerant) effective microorganisms EM culture; and
    incubating the OMP with the EM under suitable condition and at defined period to provide a bioaugmented OMP;
  preparing a sugar based organic emulsion (OE);
  providing a bioaugmented organic material preparation (OMP) inoculated with an acclimatized (preferably halotolerant) effective microorganism (AEM) by;
    inoculating the bioaugmented OMP in a high salt concentration fertilizer or in a sugar-based OE in defined ratio in stepwise manner with increasing concentration and incubating under suitable condition and for a period sufficient, as described herein, to provide bio-augmented OMP inoculated with acclimatized EM;

blending the bio-augmented OMP inoculated with AEM, with a target fertilizer and binding, coating or granulating the target fertilizer with the bio-augmented OMP inoculated with AEM to provide bioaugmented fertilizer with AEM.

In some embodiments, the method may further comprise coating the bioaugmented fertilizer with AEM, by applying another fertilizer and carrying out coating or granulation to provide powder or granular fertilizer product.

In some embodiments, the method may further comprise coating the bioaugmented fertilizer with AEM, by applying a bio-augmented organic emulsion (OE) inoculated with AEM to provide coated fertilizer product.

In some embodiments, there is provided a culture of (preferably halotolerant) effective microorganisms that may comprise the steps of:
  isolating (preferably halotolerant) microorganisms preferably from salt affected soils;
  screening and selecting effective (preferably halotolerant) nutrient mobilizing microorganisms (NMM) capable of improving the bioavailability of immobile or less mobile or mobile plant nutrients to the plant;
  screening and selecting effective (preferably halotolerant) plant growth regulating microorganisms (PGRM) capable of regulating plant growth;
  growing selected NMM and PGRM separately; and
  optionally mixing cultures of NMM and PGRM and providing a culture of (preferably halotolerant) effective microorganisms EM.

In some embodiments, the step of providing the bio-augmented organic material preparation (OMP) may comprise:
  providing Organic matter prepared (OMP);
  inoculating the OMP with the (preferably halotolerant) effective microorganisms EM culture; and
  incubating the OMP with the EM under suitable condition and at defined period to provide a bioaugmented OMP.

In some embodiments, the Organic matter prepared (OMP) may be prepared by the process that may comprise:
  selecting suitable organic matter for example plant or animal solid waste, humic acid or the like;
  drying the organic matter and separating any undesired material; and
  converting the dried organic matter to 300-400 mesh by grinding at a temperature not exceeding 30-40° C.

In some embodiments, the step of providing the bio-augmented organic material preparation (OMP) inoculated with AEM may comprise:
  inoculating the OMP with the (preferably halotolerant) effective microorganisms EM culture to provide a bioaugmented OMP;
  incubating the culture comprising the EM and OMP, with a high salt concentration fertilizer to acclimatize the EM;
  screening, isolating and cultivating the acclimatized EM (AEM); and
  inoculating the AEM bio-augmented organic material preparation (OMP) inoculated with
  storing in OMP.

In some embodiments, the step of providing an oil emulsion (OE) for coating and or binding may comprise:
  selecting an organic binder rich in sugar as an aqueous phase;
  selecting an oil or wax based moisture protector as an oil phase; and
  mixing the aqueous phase and the oil phase and emulsifying by homogenizing the mixture in a suitable equipment, at a suitable mixing speed and condition, for a period sufficient to provide the OE.

In some embodiments, the step of providing a bioaugmented oil emulsion (OE) inoculated with AEM may comprise the steps of:
  preparing an organic emulsion (OE) of a sugar based organic binder with an oil or wax based moisture protectant;
  inoculating OE with (preferably halotolerant) effective microorganisms EM culture to provide a bioaugmented OE;
  gradually changing the ratio of OE and EM to desired target OE concentration for achieving acclimatized EM (AEM);
  isolating the AEM after achieving target acclimatization level; and
  providing the bio-augmented organic emulsion (OE) inoculated with AEM;
  cultivating the acclimatized AEM and storing in OE.

In some embodiments the bio-augmented OE inoculated with AEM may be used for binding/coating of bio-augmented OMP inoculated with AEM. The bio-augmented OE inoculated with AEM may be used in specific dose for properly binding/coating of bio-augmented OMP inoculated with AEM for different types of target fertilizer for example ranging between 0.1-20% of the coated material.

In some embodiments, the present disclosure may include an integrated process of bioaugmentation of organic matter prepared (OMP) and acclimatization of (preferably halotolerant) effective microorganisms (EM) in high concentration of oil emulsion (OE), the process may comprise the steps of:
  taking bioaugmented OMP and OE in defined ratio and incubating under suitable condition in presence of microbial growth promoting nutrients and for a period sufficient to acclimatize the EM comprised in the bioaugmented OMP;
  changing step wise the ratio of bioaugmented OMP and OE sequentially by increasing the concentration of OE and in each step incubating the mixture under suitable condition in presence of microbial growth promoting nutrients and for a period sufficient to achieve desired level of acclimatization the EM population in OE.

In accordance with the disclosure, the enrichment or inoculation of AEM may improve the bioavailability of plant nutrient elements applied through fertilizer to the soil, especially those that get fixed or become unavailable/less-available to plants due to chemical/physical/biological properties of the soil, such as the presence of Phosphorus, Zinc, Copper, Potassium, Sulfur, etc.

The enrichment or coating of OMP may improve the bioavailability of plant nutrient elements applied through fertilizer to the soil, especially those that are highly mobile, e.g., Nitrogen and Sulfate, etc., by providing an organic absorption/adsorption material close to fertilizer granule/particle.

The enrichment or coating of OE may improve the bioavailability of plant food nutrient elements applied through fertilizer, especially the fertilizers that are highly soluble like Urea, Calcium Ammonium Nitrate (CAN), etc., by optimizing quick moisture penetration in fertilizer granule/particle after application to the soil.

The enrichment or coating of OE may improve the physical properties of fertilizer, i.e., free-flowing, storability, reduction in fine/powder production during storage, especially in case of Urea, CAN etc.

The following description of the specific embodiments are included to further illustrate working of the present disclosure in combination with the figures and not intended to take restrictively to imply any limitations on the scope of the present disclosure.

As shown if FIG. 1, the overall process flow of technology is elucidated in generally at 100. Two separate processes of acclimatization of selected and isolated strains (as further described in FIGS. 10 and 11) may merge at different stages as shown in FIG. 12. These two acclimatizations may be separate processes, independent of one another. They can be scaled such that the entire yield of the separate processes, or a portion thereof, may be used in the subsequent steps of the overall process. If only a portion of the yield is used, the remaining can be stored and used in a later iteration of the overall process.

As shown in FIG. 2, and referring back to FIG. 1, another, one of the independent processes 200 may be the isolation and preparation of large quantities of (preferably halotolerant) nutrient mobilizing microorganisms (NMM) and plant growth regulating microorganisms (PGRM) collectively known as EM. FIG. 2 shows an exemplary detailed flowchart of the process shown generally at 120 of FIG. 1. As shown, isolation, identification and selection of EM for nutrient mobilizing and plant growth regulating microorganisms may be accomplished through two intermediary steps (1) isolation and selection of EM and (2) commercial production of separate inoculum of each EM.

As to the first intermediary step 210 for isolation and selection of efficient NMM and PGRM, rhizosphere soil may be collected from crop fields, preferably from problematic soils, for example saline, sodic, saline-sodic, or waterlogged soils with high salt levels. Crop plants may be uprooted at different growth stages and brought to the laboratory in pre-sterilized polythene bags. Non-rhizosphere soil may be removed by agitating the roots strongly. Soil strictly adhering to the roots may be used for isolation of Rhizo-microbes, which may then be isolated by employing a serial dilution plates technique (Zuberer, 1994; Semedo, et al., 2001; Shahzad, et al., 2010). For this, target nutrient enriched media (NEM) were used such as rock phosphate for Phosphorus, elemental zinc for Zinc, and elemental sulfur for Sulfur, etc., for NMM and 1-aminocyclopropane-1-1carboxylate (ACCA) enriched media (ACCEM) for PGRM. Colonies exhibiting prolific growth may be selected for further streaking on fresh plates of the respective medium. Further purification and multiplication of microbial isolates may be performed by re-streaking on fresh plates of the respective medium (NEM and ACCEM). The isolated NMM may then be examined for nutrient mobilizing potentials and PGRM for ACC deaminase activity (ACCDA). Forty (40) mL of the sterilized respective broth of NEM and ACCEM may be added to two autoclaved test tubes respectively. The media may then be inoculated with the NMM and PGRM, respectively and incubated between at 25° C. to 35° C. temperature. An un-inoculated test tube may be used as a control. The NMM showing maximum target nutrient mobilization and PGRM showing maximum ACCDA are selected for further studies. Culturing conditions for maximized growth of NMM, nutrient mobilizing activity, PGRM and ACCDA may thereafter be optimized. The optimal conditions for NMM and PGRM generally may be between 25° C. to 38° C. at a pH close to neutral, with an incubation period of 50-96 hours under continuous shaking.

As per the method and process shown in FIG. 2, the nutrient mobilizing capability of NMM may be observed based on qualitative analysis 220 and quantitate analysis 230. In addition, ACCDA of the PGRM isolates may be observed based on a qualitative analysis 240. Potential of NMM to mobilize nutrient(s) based on qualitative analysis 220 may be performed by using the following preferred method and process: An agar medium may be prepared wherein a single nutrient source, e.g., Rock phosphate or insoluble Zinc or elemental Sulfur may be used. NMM may be tested by observing a halo zone formation. NMM may first be cultured in broth for three to five days. Thereafter, culture of each NMM may be spotted on their respective agar plate with the help of sterilized toothpicks, plates may be incubated at 25° C. to 38° C. for six to ten days. The formation of halo zones after 50-96 hours of incubation indicates the NMM ability to mobilize nutrient from an inorganic source. The experiment is repeated three times to ensure consistent replication.

Optimizing the potential of NMM to mobilize inorganic source on the basis of quantitative analysis 230 may be performed by using the following method and process: A mathematical analysis of nutrient mobilizing activity of NMM may be determined by the methods described by Nautiyal (1999). An inorganic nutrient source, e.g., rock phosphate, elemental Sulfur, elemental Zinc, or any other nutrient carrying mineral may be used in broth medium. Quantitative estimations may be based on concentration of specific nutrient mobilization in broth medium inoculated with selected NMM in triplicate. An autoclaved un-inoculated medium may be run as a control. Flasks containing insoluble nutrient source and respective NMM may be incubated for two to five days at 25° C. to 38° C., in an orbital shaking incubator. The cultures may then be harvested after centrifugation at 8,000 to 10,000 rpm. The respective supernatant may be analyzed for soluble phosphate, for example as described by Ryan, et al. (2001), and for sulfur protocol, for example as described by Tabatabai, et al. (1998).

Optimizing the potential of PGRM for ACCDA based on qualitative analysis 240 may be determined by using the following method and process: DF minimal medium may be prepared as per protocol described by Dworkin and Foster (1958) and supplemented with ACC as the sole source of nitrogen (Penrose and Glick, 2003). Solid DF minimal medium containing ACC may be inoculated with a loop full of starter culture (grown overnight in LB broth at 25° C. to 38° C. in orbital shaking incubator). Plates may be incubated at 25° C. to 38° C. in darkness. When a colony emerges within two to four days that indicates the existence of ACCDA.

Potential of PGRM for ACCDA based on a quantitative analysis 260 may be performed by using the following process: Quantitative determination of ACCDA of PGRM may be done by measuring the production of alfa-ketobutyrate from ACC. Liquid DF minimal salt medium containing ACC may be inoclutated with PGRM and incubated at 25° C. to 38° C. for 56-96 hr. Then the culture may be centrifuged at 8,000 to 10,000 rpm and a microbial pallet may be obtained. The production of alfa-keto-butyrate may be measured by using the regent 2, 4-dinitrophenylehdrazine, following the protocol described by Penrose and Glick (2003).

Referring back to FIG. 2, the second step is the commercial production of the separate inoculum containing NMM and PGRM 260. This may be accomplished by separately growing NMM and PGRM in two different steps using the same growing medium1 220. Thereafter, the same inoculum of NMM and PGRM may be prepared by using media in two different containers for commercial production 270. In other words, the basic breeding media may be cultivated. Then in the second step, commercial media may be used for large scale biomass production of NMM and PGRM, separately (see tables in FIGS. 3 and 4). Finally, the media (NMM and PGRM) for commercial production 270, should contain several billion microbe colonies per millimeter in order to keep the respective inoculum viable for culturing, storage and field application.

As shown in FIG. 3, the F1 breeding for 100 mL of the medium 1, 160 may be prepared in two different containers for NMM and PGRM, separately, using mannitol, KH2PO4, yeast extract, and MgSO4 maintaining pH levels of 6.0 to 7.5. The entire mixture may then be autoclaved. Thereafter the selected strains of NMM and PGRM may be mixed in their respective containers when the temperature drops to normal. The flasks may be incubated at 25° C. to 35° C., for example by continuous shaking on an orbital shaker. The desired population may be achieved within fifty to ninety-six hours that can be checked by measuring optical density (OD) through UV-visible spectrophotometer.

As shown in FIG. 4, the media for commercial production 170 may be prepared in two different containers for NMM and PGRM, separately. For this H2O, trypton, calcium pantothenate, yeast extract, B1, KH2PO4, and Vitamin B12 may be used to maintain pH levels at 6.5-7.5. The pH should be adjusted to the target range, for example by adding a few drops of H2SO4 or NaOH. The entire mixture may then be autoclaved. Thereafter, the selected strains of NMM and PGRM may be mixed in the respective containers when the temperature gets normal. The flasks may be incubated at 25° C. to 35° C. temperature under shaking conditions and continuous aeration. The desired population may be achieved in 50-96 hours that can be checked by measuring OD through UV-visible spectrophotometer.

Referring to FIG. 5, diagram 500 shows eight exemplary factors that may be optimized during bio augmentation and acclimatization in light of variables such as fertilizer material, bio-coating emulsion, soil type, organic matter, and climate. These may include target fertilizer granule and bioaugmented OMP ratio 510, organic emulsion and EM solution ratios 560, incubation period 530, moisture 570, temperature 540, N-source 580, microbial population count and ACCDA production capacity 550, and carbon source 590.

As shown in FIG. 6, a diagram shows another example of the independent processes includes the step of selection and preparation of organic material referred to as organic matter prepared (OMP) 600 for use in later EM acclimatization with respect to high salt level and OE. An exemplary flowchart is shown in FIG. 6. selection of a suitable source of organic matter (OM) is the first step 610. Examples of suitable organic matter may include press mud from sugar industry, by-products of the citrus juice industry, vegetable waste, fruit waste, poultry manure, humic acid, seaweed extract enriched OM, farmyard manure, and other compostable plant and animal materials, etc. The choice of OM may also depend on the possible interactions of the OM with the target fertilizer and EC.

In step 620, the selected OM may be exposed to air at 80° C. temperature for sufficient time to dry and remove any contaminating microorganisms. The dried OM may be sieved to remove unwanted matter in step 630 and then ground to 300-400 mesh size in step 640. The clean finely ground organic matter prepared (OMP) may be stored in heat-sealed polyethylene (PE) bags under ambient conditions in step 650 to avoid contamination or deterioration. This OMP may be to be used in later steps.

As shown exemplary flowchart 700 in FIG. 7, selection and preparation of the target nutrient element supplementing fertilizer process may be given in step 710. The target material may be dried, for example with 30-60° C. hot air in rotary drum moving at 30-40 r.p.m. for 20-60 minutes. Test moisture level may be kept less than 0.5-1.5%. Fertilizer granules of 2-3 mm size may be produced through multiple mesh size sieving machine. If in powder form, the fertilizer may be converted to granules of 2-3 mm, for example by using OE or other suitable binder (step 720). Care may also be taken that the fertilizer material is free from dust. It may then be packed in polythene lined bags to avoid any moisture insurgence (step 730). Uniformity in granule size may help in improving the acclimatized EM.

Referring back to FIG. 1 at step 150 Bio augmented OMP is described. It may be prepared through process shown in FIG. 8.

As shown in FIG. 8, an exemplary process 800 for bioaugmentation of OMP is elucidated. At step 810: OMP prepared through process shown in FIG. 6 may be taken in known quantity.

Simultaneously at step 860 of FIG. 8, selected, isolated, commercially multiplied and properly stored EMs through the process of FIG. 2 may be taken in known quantity.

At step 820 of FIG. 8, OMP may be mixed with the commercially produced EMs. The ratio of OMP and EM may be 95:5 or other and both may be placed in stainless steel rotary mixer. The rotary mixer may be moved at 5-10 r.p.m. for 10-15 minutes every three hours for 2-3 days. The temperature may be monitored and beyond 40° C. drum rotation frequency may be altered to keep it to the required level. The population of EM may be monitored at known intervals and the process may continue till the desired OMP population density of 109 per g is achieved.

At step 840 of FIG. 8, the EM Bio augmented OMP may be dried, for example with dry air of 30-40° C. temperature to bring the moisture to less than 5% level. The dried Bio augmented OMP may be packed in aluminum foil packing and sealed with heat to ensure zero moisture penetration (step 850).

Referring once again to FIG. 1, the process may include another independent process step 110, Organic Emulsion (OE).

OE is a complex mixture of organic binder, wax/lubricant and carbon source, which may serve as a binding agent, anticaking, and a source of energy for EM. This OE inoculated with EM may improve product shelf life, reduce lump formation and powder emergence. Its wax may reduce volatilization losses, as it checks water penetration into highly hygroscopic fertilizers such as Urea and CAN etc. An exemplary flowchart of the OE process preparing is shown in FIG. 9.

As shown in FIG. 9, in some embodiments, a method 900 for preparing oil emulsion (OE) is illustrated. OE may be prepared by selecting organic binder such as sugar, fine ground gum of plant origin (step 910), wax, or oil (step 930). The appropriate ratios of all ingredients of OE may depend on the type of fertilizer and the use of OE, i.e., for coating or binding.

In FIG. 9, OE ingredients may be selected and mixed in a variable ratio, and may be placed in a water-cooled vertical multilevel blade homogenizer (step 920). Cool water may be made to flow over the outer shell of the homogenizer to keep the temperature between 30-35° C. during the contents mixing process. The materials may be heated to 35° C. in step 940 and blended at high speed for 10 to 15 minutes in step 950. After blending, the mixture may become homogenous and stable. A surfactant, such as sticky sugar industry waste, can be used to keep the homogenous mixture from separating during storage. In step 960, the prepared outer coating material may be stored in a suitable container and sealed to prevent moisture absorption, contamination, and quality deterioration.

As shown in FIG. 10, one of the independent processes is shown for the acclimatization of EM in a high concentration of OE.

In FIG. 10 one embodiment is the overall process of EM acclimatization in OE having high sugar and fats levels, as described in FIG. 9 as a multistage or multistep process. It may be an independent process that merges with other processes during preparation of the final product (FIG. 12 processes).

In FIG. 10 at step 1010, EM commercial solution may be taken in a known quantity required for Bioaugmented of OMP and OE.

At step 1020 of FIG. 10, a known quantity of OE may be taken prepared through the process given in FIG. 9.

At step 1025, EM commercial solution and OE may be taken at a ratio of 90-95:10-5 in vertical, multilevel, bladed homogenizer having a stainless-steel body. The homogenizer is operated at 300-400 RPM for 10-15 minutes.

At step 1030, the homogenized mixture of EM and OE (mixed in step 1025) may be transferred to an incubator. During incubation period, mixture may be exposed to extreme temperature variation, for example three times a day. First it may be kept at 500° C. for fifteen minutes and then at 100° C. for fifteen minutes. This extreme temperature exposure may be carried out three times a day. During the rest of the time, the temperature may be maintained at 30±2° C. This temperature exposure may be carried out, for example for 2 days in an incubator. At step 1035, during incubation, EM growth promoting materials such as carbon and nutrients sources may be added as per known quantity. Nutrient mix and type is described in FIG. 4. At step 1015, the mixture may be regularly monitored for EM population and qualitative performance, as per procedures described in FIG. 2. The incubation period can be increased or decreased in order to attain the EM population of 109 per mL.

At step 1040, EM commercial solution and OE ratios of the mixture, produced during step 1030, may be changed to 85-90:15-10. EM and OE solution may be mixed and homogenized in vertical, multilevel, bladed homogenizer having a stainless-steel body. The homogenizer may be operated at 300-400 r.p.m. for 10-15 minutes.

At step 1045, homogenized mixture of EM and OE (prepared during step 1040) is transferred to an incubator and same process is adopted as described in step 1030.

At step 1050, EM commercial solution and OE (produced through step 1045) ratios may be changed to 80-85:20-15. EM and OE solution may be mixed and homogenized in vertical, multilevel, bladed homogenizer having a stainless-steel body. The homogenizer may be operated at 300-400 RPM for 10-15 minutes.

At step 1055, the homogenized mixture of EM and OE (mixed in step 1045) may be transferred to an incubator and same process may be adopted as described in step 1030.

At step 1060, the homogenized mixture of EM and OE (mixed and incubated at step 1055) may be packed in dark color plastic or mild steel containers lined with Epoxy coating for commercial production of Acclimatized EM (AEM) bio-augmented fertilizer.

As shown in FIG. 11, as per one embodiment, the overall process of EM acclimatization in a high salt environment is described. It may be a multistage or multistep process. It may be an independent process and merges with overall processes during preparation of the final product (FIG. 12 process).

As per step 1110, target quantity of bio-augmented OMP may be taken, which was prepared through the process described in FIG. 8.

At step 1120, target fertilizer may be taken which was produced through the process given in FIG. 9.

The target quantity of fertilizer and Bioaugmented OMP may depend on the ultimate ratio of fertilizer and bio-augmented OMP.

At step 1125, bio-augmented OMP and fertilizer may be mixed at 70-90:30-10 ratio in stainless steel rotary drum. The rotary drum may be operated at 2 rpm. for thorough mixing of the two materials, for example for 15-30 minutes.

At step 1130, bio-augmented OMP and fertilizer mixed in step 1125 may be transferred to an incubator. The temperature of the incubator may be maintained at 30±2° C., for example for three days. During incubation period, mixture may be exposed to extreme temperature variation three times a day. First mixture may be kept at 50° C. for 15 minutes and then at 10° C. for 15 minutes. During the rest of the time, the temperature is maintained at 30±2° C. This temperature exposure is carried out for 2 days in an incubator. At step 1160 during incubation, EM growth promoting materials such as carbon or nutrients sources of known quantity may be added. The nutrient mix and type is described in FIG. 4. At step 1115, the mixture may be regularly monitored for EM population and qualitative performance as per procedures described in FIG. 2. The incubation period can be increased or decreased so that the EM population becomes 109/g.

At step 1135, the mixture produced at step 1130 of FIG. 11 may be transferred to a rotatory drum. Bio-augmented OMP and fertilizer ratio may be changed to 40-60:40-60 in stainless steel rotary drum. The rotary drum may be operated at 2 r.p.m for thorough mixing of the two materials, for example for 15-30 minutes.

At step 1140, bio-augmented OMP and fertilizer mixed in step 1135 may be transferred to an incubator. The temperature of the incubator may be maintained at 30±2° C., for example for three days. During incubation period, mixture may be exposed to extreme temperature variation three times a day. During the rest of the time, the temperature may be maintained at 30±2° C. This extreme temperature exposure may be applied for 2 days in an incubator. At step 1160, during incubation EM growth promoting material such as carbon or nutrients sources of known quantity may be added. The nutrient mix and type is described in FIG. 4. At step 1115, the mixture may be regularly monitored for EM population and qualitative performance as per procedures described in FIG. 2. The incubation period can be increased or decreased to gain an EM population of 109.

At step 1145, the mixture of bio-activated OMP and fertilizer produced at step 1140 may be transferred to a rotatory drum. Bio augmented OMP and fertilizer ratio may be changed to 10-20:90-80in stainless steel rotary drum. The rotary drum may be moved at 2 RPM for thorough mixing of the two material for 15-30 minutes.

At step 1150, bio-augmented OMP and fertilizer mixed in step 1145 may be transferred to an incubator. The temperature of the incubator may be maintained at 30±2° C., for example for three days. During incubation period, mixture may be exposed to extreme temperature variation three times a day. During the rest of the time, the temperature may be maintained at 30±2° C. This extreme temperature exposure may be applied for 2 days in an incubator. As per step 1160, during incubation with EM growth promoting material like carbon or nutrients sources of known quantity may be added. The nutrient mix and type is described in FIG. 6. At step 1115, the mixture may be regularly monitored for EM population and qualitative performance as per procedures described in FIG. 2. The incubation period can be increased or decreased to get 109/gm EM population.

At step 1155, bio-augmented OMP and fertilizer incubated in step 1150 may be separated through appropriate size mesh sieve. The bio-augmented OMP having a population of acclimatized EM around 109 may be dried to a moisture level of 1-2% with dry air of 30° C. temperature. This dried material may be mixed in a rotary drum with fresh OMP at 50:50 or any other appropriate ratio. The rotary drum may be moved at 2 RPM for 30 minutes. This material may be packed in Polythene airtight bags. These bags may be kept in a dark place for two months and then used in commercial production of Acclimatized EM (AEM) fertilizer.

As shown in FIG. 12, as per one embodiment, the overall process of manufacturing AEM bioaugmented fertilizer through coating, mixing, or binding the variable fertilizers may be provided. In the process, two types of acclimatized AEM carrying material produced through the processes given in FIGS. 10 and 11 may be used. EM may be acclimatized with high salt level (fertilizer) produced through the process of FIG. 10 and another type of acclimatized EM with EC may be produced through the process given in FIG. 11. Each type of AEM can be used jointly or alone. The coating/mixing of both AEM converts the fertilizer into AEM bio-augmented fertilizer. AEM bio-augmented fertilizer improves efficacy of plant nutrients, which normally convert into immobilize or less immobilize form after dissolving into the soil.

As shown in FIG. 12, overall production processes may be common with a minor change in the physical property of the target fertilizer, i.e., from powder to granular form. In order to exhibit the basic process, details FIG. 12 are described.

In FIG. 12 at step 1220, the target quantity of fertilizer in granule may be taken and sieved to have free-flowing product. Removal of lumps or impurity improves homogenous mixing and coating of AEM enriched OMP and OE.

At step 1210, the target quantity of AEM Bio augmented OMP, prepared as per the FIG. 11 process, may be taken.

At step 1230, the target fertilizer granule and AEM bio-augmented OMP may be loaded in stainless steel mixing/granulation rotary drum. 25% quantity of target fertilizer prepared at step 1220 may be loaded in mixing/granulation drum and then 25% quantity of AEM bio-augmented OMP measured at step 1210 may be loaded. Similarly, both the ingredients (fertilizer and AEM bio-augmented OMP) may be mixed in four installments. This layering ensures homogenous mixing and uniform spread of AEM. The rotary drum may be operated at 3-5 RPM till the entire material may be homogenously mixed. It may be ensured that the loading/unloading point lid is properly closed and airtight. Proper closure of coating drum may be essential as it will create a dusty environment inside the drum due to its movement. This suspension of target material (secondary/trace element) to be coated on carrier fertilizer will ensure even coating. The rotary drum may be kept idle for 3-5 minutes while intact during loading and unloading. This allows the suspended particles to settle down.

At step 1240, AEM bio-augmented OE may be taken in target quantity required for one batch coating. It may be loaded into stainless steel dispensing machine storage tank. The AEM enriched OE dispensing machine includes the following inbuilt systems:
  thermostat control heating system
  homogenizer in the storage tank
  high-pressure rotary pump
  graduated quantity controller dispenser
  pressure hosepipe
  hollow cone spraying nozzle fixed inside at the top of the rotary drum.

The target quantity may be mixed for 3-5 minutes at 30-40° C. temperature and the rotary pump may be set to provide 20-25 PSI pressure through the hose pipe.

At step 1240, the mixture of fertilizer and AEM enriched/inoculated OMP may be rotated at 2-5 RPM. At step 1250, spray of bioaugmented OE inoculated with AEM may be done simultaneously through dispensing machine. The spraying of bioaugmented OE inoculated with AEM may be carried out till the entire material inside the rotary drum may be coated/converted into granules or mixed properly in case if target product/s are powder.

At step 1260, dry air may be supplied to the coated/granulated/mixed material (target fertilizer) for enough time to make the product dry.

At step 1270, the AEM coated/granulated product may be packed in woven polythene bags lined with appropriate strength plastic liner. It may be also ensured that the product is stored in a dark and dry place before use.

FIGS. 13A and 13B show exemplary cross sections/diagrams of different coated/granulated/mixed products bio-augmented with OMP and OE inoculated with AEM and/or other fertilizer, according to some embodiments of the present disclosure. In FIG. 13A, a cross section of granular fertilizer, an end product is depicted produced through coating/granulation. It comprises major carrier fertilizer, Bioaugmented OMP inoculated with AEM, Bioaugmented OE inoculated with AEM and second/multiple powder fertilizers are depicted. A bioaugmented product can be coated/granulated with all three ingredients or with OMP & OE inoculated. In FIG. 13B, another cross section is depicted to describe cross section of powder Bioaugmented fertilizer/s with AEM having fertilizer/s, Bioaugmented OMP enriched with AEM with or without OE inoculated with AEM.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

As used herein and in the appended claims, the singular forms "a," "an," and "the" include plural referents unless the context clearly dictates otherwise.

In general, terms such as "coupled to," and "configured for coupling to," and "secure to," and "configured for securing to" and "in communication with" (for example, a first component is "coupled to" or "is configured for coupling to" or is "configured for securing to" or is "in communication with" a second component) are used herein to indicate a structural, functional, mechanical, electrical, signal, optical, magnetic, electromagnetic, ionic or fluidic relationship between two or more components or elements. As such, the fact that one component is said to be in communication with a second component is not intended to exclude the possibility that additional components may be present between, and/or operatively associated or engaged with, the first and second components.

In the above description and in the figures, like elements are identified with like reference numerals. The use of "e.g.," "etc.," and "or" indicates non-exclusive alternatives without limitation, unless otherwise noted. The use of "including" or "includes" means "including, but not limited to," or "includes, but not limited to," unless otherwise noted.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" can refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

What is claimed is:

1. A bioaugmented fertilizer with acclimatized effective microorganism(s) (AEM), comprising:
   one or more target fertilizer;
   a target fertilizer specific AEM consortium;
   organic elements bio-augmented with the AEM; and
   organic emulsion (OE) bioaugmented with AEM, wherein the OE bioaugmented with AEM is configured to coat the bioaugmented fertilizer with AEM.

2. The bioaugmented fertilizer with acclimatized effective microorganism(s) (AEM) of claim 1 further comprises an organic emulsion (OE) with or without bioaugmentation with AEM, providing an Integrated Plant Nutrient Management (IPNM).

3. The bioaugmented fertilizer with acclimatized effective microorganism(s) (AEM) of claim 2, wherein the OE improves:
   the bioavailability of soluble plant nutrient supplementing fertilizers; and
   the physical properties of the bioaugmented fertilizer including free-flowing, storability and reduction in powder production while storage.

4. The bioaugmented fertilizer with acclimatized effective microorganism(s) (AEM) of claim 1, wherein the AEM improves bioavailability of unavailable or less-available plant nutrient elements applied by the bioaugmented fertilizer to the soil.

5. The bioaugmented fertilizer with acclimatized effective microorganism(s) (AEM) of claim 1, wherein the bioaugmented organic elements retain plant nutrients.

6. A method of producing a bioaugmented fertilizer with acclimatized effective microorganism (AEM), comprising the steps of:
   providing a culture of effective microorganisms (EM) by:
      isolating microorganisms from salt affected soils,
      screening nutrient mobilizing microorganisms and plant growth regulating microorganisms,
      culturing the screened nutrient mobilizing microorganisms and the plant growth regulating microorganisms separately, and
      mixing cultures of the screened nutrient mobilizing microorganisms and the plant growth regulating microorganisms to provide a culture of effective microorganisms (EM);
   preparing a bio-augmented organic matter prepared (OMP) by:
      providing an Organic Matter Prepared (OMP), wherein the OMP is prepared by selecting an organic matter from at least one of plant or animal origin, drying the organic matter and separating a portion of the organic matter from the dried organic matter, and converting the dried organic matter to 300-400 mesh by grinding at a temperature not exceeding 40° C.,
      inoculating the OMP with the effective microorganisms EM culture, and
      incubating the OMP with the EM under a condition and at a defined period to provide a bioaugmented OMP;
   preparing an organic emulsion (OE), wherein the OE is a complex mixture of organic binder, wax/lubricant and a carbon source;
   providing the bioaugmented organic matter prepared (OMP) inoculated with an acclimatized effective microorganism (AEM) by:
      inoculating the bioaugmented OMP in a salt concentration fertilizer or in the OE in defined ratio in stepwise manner with increasing concentration and incubating under a target condition and for a defined period sufficient to provide a bio-augmented OMP inoculated with acclimatized EM; and
   blending/coating/granulating the bioaugmented OMP inoculated with AEM, with a target fertilizer/s EM, to provide a bioaugmented fertilizer with AEM.

7. The method of claim 6, wherein the bioaugmented organic matter prepared (OMP) inoculated with AEM by the process comprising:
   inoculating the OMP with the effective microorganisms (EM) culture to provide a bioaugmented OMP;
   incubating the culture comprising the EM and OMP, with a salt concentration (fertilizer) to acclimatize the EM;

screening, isolating and cultivating the acclimatized EM to have Acclimatized Effective Microorganisms (AEM); and inoculating the AEM with organic matter prepared (OMP) and storing the OMP inoculated with AEM.

8. The method of claim 7, wherein the bioaugmented oil emulsion (OE) inoculated with AEM is prepared by the process comprising the steps of:
  inoculating the OE with effective microorganisms EM culture to provide a bioaugmented OE;
  gradually changing the ratio of OE and EM to a predetermined target OE concentration for achieving acclimatized EM to AEM;
  isolating the AEM after achieving a target acclimatization level;
  providing the bioaugmented organic emulsion (OE) inoculated with AEM; and
  cultivating the acclimatized AEM and storing the OE inoculated with AEM.

9. The method of claim 8, further comprising:
  using a quantity of OM inoculated AEM produced in claim 7;
  using a quantity of OE inoculated AEM produced in claim 8;
  blending the bioaugmented organic matter prepared (OMP) inoculated with AEM of claim 7 with a target fertilizer/s at a target ratio;
  coating the target fertilizer/s with the bio-augmented organic emulsion (OE) inoculated with AEM of claim 8 to provide a bioaugmented fertilizer with AEM at the target ratio; and
  performing granulation of the target fertilizer/s with bio-augmented organic matter prepared (OMP) inoculated with AEM of claim 7 and the OE inoculated AEM of claim 8 at the target ratio and a target size.

10. The method of claim 6, further comprising a granulation of target powder fertilizer/s by mixing of target fertilizer/s, Bioaugmented OMP with AEM with or without bio-augmented OE inoculated with AEM.

11. The method of claim 6, further comprising coating the bioaugmented OMP inoculated with AEM and/or powder fertilizers on granular carrier fertilizer by applying a bio-augmented organic emulsion (OE) inoculated with AEM to provide a coated bioaugmented fertilizer product.

12. The method of claim 6, wherein the method further comprises mixing target fertilizer/s, bioaugmented OMP inoculated with AEM to provide a blended bioaugmented fertilizer product.

13. The method of claim 6, wherein the oil emulsion (OE) for coating and/or binding is prepared by the process comprising:
  selecting an organic binder rich in sugar as an aqueous phase;
  selecting an oil or wax based moisture protector as an oil phase; and
  mixing the aqueous phase and the oil phase and emulsifying by homogenizer, at a defined mixing speed and condition and time to provide a stable OE.

* * * * *